United States Patent
Skutnik et al.

(10) Patent No.: US 9,782,536 B2
(45) Date of Patent: Oct. 10, 2017

(54) INFUSION SET AND/OR PATCH PUMP HAVING AT LEAST ONE OF AN IN-DWELLING RIGID CATHETER WITH FLEXIBLE FEATURES AND/OR A FLEXIBLE CATHETER ATTACHMENT

(75) Inventors: Peter Skutnik, Midland Park, NJ (US); Joshua Horvath, Sparta, NJ (US); Robert Banik, Long Valley, NJ (US); Gary Searle, Norfolk, MA (US); Eric Bene, Lynn, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 189 days.

(21) Appl. No.: 13/138,128

(22) PCT Filed: Jan. 11, 2010

(86) PCT No.: PCT/US2010/000054
§ 371 (c)(1),
(2), (4) Date: Sep. 1, 2011

(87) PCT Pub. No.: WO2010/080715
PCT Pub. Date: Jul. 15, 2010

(65) Prior Publication Data
US 2011/0313357 A1    Dec. 22, 2011

Related U.S. Application Data

(63) Continuation-in-part of application No. 12/585,061, filed on Sep. 2, 2009, now Pat. No. 9,375,529.
(Continued)

(51) Int. Cl.
*A61M 5/168* (2006.01)
*A61M 5/142* (2006.01)
(Continued)

(52) U.S. Cl.
CPC ........ *A61M 5/14248* (2013.01); *A61M 5/158* (2013.01); *A61M 5/46* (2013.01);
(Continued)

(58) Field of Classification Search
CPC ............ A61M 25/007; A61M 25/0071; A61M 25/0097; A61M 2025/0098
(Continued)

(56) References Cited

U.S. PATENT DOCUMENTS

| 3,599,641 A | 8/1971 | Sheridan |
| 3,857,382 A | 12/1974 | Williams, Jr. et al. |

(Continued)

FOREIGN PATENT DOCUMENTS

| EP | 0980687 A2 | 2/2000 |
| EP | 1044374 B1 | 10/2008 |

(Continued)

*Primary Examiner* — Laura Bouchelle
(74) *Attorney, Agent, or Firm* — Dickinson Wright PLLC

(57) ABSTRACT

An infusion set, patch pump, or elements thereof, having an exemplary catheter (14) provided with one or more channels, grooves and coatings (24, 34, 44), configured and arranged to provide a degree of strength and flexibility. The catheter (14) can also have an exemplary flexible union with the hub (12) having at least one of a ball-and-socket joint (66, 68), a sliding plate (86), and a flexible bushing (106), and which is sealed to allow even further movement of the catheter (14) while preventing leakage of medication through the junction. In doing so, a number of benefits associated with the use of rigid materials in catheter construction can be provided while at the same time, benefits associated with the use of flexible materials in catheter construction and/or flexible engagement with the hub can also be provided.

23 Claims, 17 Drawing Sheets

Related U.S. Application Data

(60) Provisional application No. 61/144,072, filed on Jan. 12, 2009.

(51) Int. Cl.
*A61M 5/158* (2006.01)
*A61M 5/46* (2006.01)
*A61M 25/00* (2006.01)
*A61M 39/10* (2006.01)
*A61M 39/12* (2006.01)
*A61M 5/14* (2006.01)

(52) U.S. Cl.
CPC ...... *A61M 25/007* (2013.01); *A61M 25/0009* (2013.01); *A61M 5/1408* (2013.01); *A61M 25/0017* (2013.01); *A61M 39/1055* (2013.01); *A61M 39/12* (2013.01); *A61M 2005/1581* (2013.01); *A61M 2005/1583* (2013.01); *A61M 2005/1585* (2013.01); *A61M 2005/1587* (2013.01); *A61M 2025/0046* (2013.01)

(58) Field of Classification Search
USPC .................................. 604/151, 174, 265
See application file for complete search history.

(56) References Cited

U.S. PATENT DOCUMENTS

| | | | |
|---|---|---|---|
| 3,918,355 | A | 11/1975 | Weber |
| 3,963,380 | A | 6/1976 | Thomas, Jr. et al. |
| 4,204,538 | A | 5/1980 | Cannon |
| 4,280,500 | A | 7/1981 | Ono |
| 4,327,722 | A * | 5/1982 | Groshong et al. ............ 604/510 |
| 4,490,141 | A | 12/1984 | Lacko et al. |
| 4,549,879 | A * | 10/1985 | Groshong et al. ............ 604/247 |
| 4,580,551 | A | 4/1986 | Siegmund et al. |
| 4,685,902 | A | 8/1987 | Edwards et al. |
| 4,723,947 | A | 2/1988 | Konopka |
| 4,734,092 | A * | 3/1988 | Millerd ............ A61M 5/14248 128/DIG. 12 |
| 4,755,173 | A | 7/1988 | Konopka et al. |
| 4,955,861 | A | 9/1990 | Enegren et al. |
| 5,102,401 | A | 4/1992 | Lambert et al. |
| 5,176,662 | A | 1/1993 | Bartholomew et al. |
| 5,178,129 | A | 1/1993 | Chikama et al. |
| 5,226,899 | A | 7/1993 | Lee et al. |
| 5,257,980 | A | 11/1993 | Van Antwerp et al. |
| 5,453,099 | A | 9/1995 | Lee et al. |
| 5,522,803 | A | 6/1996 | Teissen-Simony |
| 5,536,249 | A | 7/1996 | Castellano et al. |
| 5,545,143 | A | 8/1996 | Fischell |
| 5,545,152 | A | 8/1996 | Funderburk et al. |
| 5,545,708 | A | 8/1996 | Onwunaka et al. |
| 5,593,390 | A | 1/1997 | Castellano et al. |
| 5,728,074 | A | 3/1998 | Castellano et al. |
| 5,755,702 | A * | 5/1998 | Hillstead et al. ............ 604/264 |
| 5,800,420 | A | 9/1998 | Gross et al. |
| 5,820,602 | A | 10/1998 | Kovelman et al. |
| 5,851,197 | A | 12/1998 | Marano et al. |
| 5,858,001 | A | 1/1999 | Tsals et al. |
| 5,858,005 | A | 1/1999 | Kriesel |
| 5,925,021 | A | 7/1999 | Castellano et al. |
| 5,957,895 | A | 9/1999 | Sage et al. |
| 5,968,011 | A | 10/1999 | Larsen et al. |
| 5,980,506 | A | 11/1999 | Mathiasen |
| 6,017,328 | A | 1/2000 | Fischell et al. |
| 6,056,718 | A | 5/2000 | Funderburk et al. |
| 6,068,615 | A | 5/2000 | Brown et al. |
| 6,074,369 | A | 6/2000 | Sage et al. |
| 6,086,575 | A | 7/2000 | Mejslov |
| 6,093,172 | A | 7/2000 | Funderburk et al. |
| 6,110,148 | A | 8/2000 | Brown et al. |
| 6,123,690 | A | 9/2000 | Mejslov |
| 6,132,400 | A | 10/2000 | Waldenburg |
| 6,175,752 | B1 | 1/2001 | Say et al. |
| 6,206,134 | B1 | 3/2001 | Stark et al. |
| 6,254,586 | B1 | 7/2001 | Mann et al. |
| 6,261,272 | B1 | 7/2001 | Gross et al. |
| 6,272,364 | B1 | 8/2001 | Kurnik |
| 6,275,717 | B1 | 8/2001 | Gross et al. |
| 6,277,627 | B1 | 8/2001 | Hellinga |
| 6,293,925 | B1 | 9/2001 | Safabash et al. |
| 6,302,866 | B1 * | 10/2001 | Marggi ........................ 604/174 |
| 6,346,075 | B1 | 2/2002 | Arai et al. |
| 6,352,523 | B1 | 3/2002 | Brown et al. |
| 6,355,021 | B1 | 3/2002 | Nielsen et al. |
| 6,387,098 | B1 | 5/2002 | Cole et al. |
| 6,391,005 | B1 | 5/2002 | Lum et al. |
| 6,485,461 | B1 | 11/2002 | Mason et al. |
| 6,520,938 | B1 | 2/2003 | Funderburk et al. |
| 6,521,446 | B2 | 2/2003 | Hellinga |
| 6,544,212 | B2 | 4/2003 | Galley et al. |
| 6,546,269 | B1 | 4/2003 | Kurnik |
| 6,551,276 | B1 | 4/2003 | Mann et al. |
| 6,558,351 | B1 | 5/2003 | Steil et al. |
| 6,565,509 | B1 | 5/2003 | Say et al. |
| 6,576,430 | B1 | 6/2003 | Hsieh et al. |
| 6,579,267 | B2 | 6/2003 | Lynch et al. |
| 6,589,229 | B1 | 7/2003 | Connelly et al. |
| 6,607,509 | B2 | 8/2003 | Bobroff et al. |
| 6,656,158 | B2 | 12/2003 | Mahoney et al. |
| 6,656,159 | B2 | 12/2003 | Flaherty |
| 6,669,669 | B2 | 12/2003 | Flaherty et al. |
| 6,692,457 | B2 | 2/2004 | Flaherty |
| 6,699,218 | B2 | 3/2004 | Flaherty et al. |
| 6,706,159 | B2 | 3/2004 | Moerman et al. |
| 6,723,072 | B2 | 4/2004 | Mahoney et al. |
| 6,740,059 | B2 | 5/2004 | Flaherty |
| 6,749,560 | B1 | 6/2004 | Konstorum et al. |
| 6,749,587 | B2 | 6/2004 | Flaherty |
| 6,768,425 | B2 | 7/2004 | Flaherty et al. |
| 6,830,558 | B2 | 12/2004 | Flaherty et al. |
| 6,830,562 | B2 | 12/2004 | Mogensen et al. |
| 6,840,922 | B2 | 1/2005 | Nielsen et al. |
| 6,852,104 | B2 | 2/2005 | Blomquist |
| 6,949,084 | B2 | 9/2005 | Marggi et al. |
| 6,960,162 | B2 | 11/2005 | Saadat et al. |
| 6,960,192 | B1 | 11/2005 | Flaherty et al. |
| 6,977,180 | B2 | 12/2005 | Hellinga et al. |
| 6,997,907 | B2 | 2/2006 | Safabash et al. |
| 7,004,928 | B2 | 2/2006 | Aceti et al. |
| 7,018,360 | B2 | 3/2006 | Flaherty et al. |
| 7,029,455 | B2 | 4/2006 | Flaherty |
| 7,052,251 | B2 | 5/2006 | Nason et al. |
| 7,064,103 | B2 | 6/2006 | Pitner et al. |
| 7,070,580 | B2 | 7/2006 | Nielsen |
| 7,083,597 | B2 | 8/2006 | Lynch et al. |
| 7,109,878 | B2 | 9/2006 | Mann et al. |
| 7,128,727 | B2 | 10/2006 | Flaherty et al. |
| 7,137,964 | B2 | 11/2006 | Flaherty |
| 7,144,384 | B2 | 12/2006 | Gorman et al. |
| 7,207,974 | B2 | 4/2007 | Safabash et al. |
| 7,214,207 | B2 | 5/2007 | Lynch et al. |
| 7,226,278 | B2 | 6/2007 | Nason et al. |
| 7,303,543 | B1 | 12/2007 | Maule et al. |
| 7,303,549 | B2 | 12/2007 | Flaherty et al. |
| 7,310,544 | B2 | 12/2007 | Brister et al. |
| 7,318,816 | B2 | 1/2008 | Bobroff et al. |
| 7,329,239 | B2 | 2/2008 | Safabash et al. |
| 7,354,420 | B2 | 4/2008 | Steil et al. |
| 7,496,392 | B2 | 2/2009 | Alarcon et al. |
| 7,517,335 | B2 * | 4/2009 | Gravesen et al. ............ 604/132 |
| 7,713,258 | B2 | 5/2010 | Adams et al. |
| 7,729,735 | B1 * | 6/2010 | Burchman .................... 600/339 |
| 8,172,803 | B2 | 5/2012 | Morrissey et al. |
| 8,221,359 | B2 | 7/2012 | Kristensen et al. |
| 8,262,618 | B2 | 9/2012 | Scheurer |
| 8,277,415 | B2 | 10/2012 | Mounce et al. |
| 8,285,328 | B2 | 10/2012 | Caffey et al. |
| 8,287,467 | B2 | 10/2012 | List et al. |
| 8,287,516 | B2 | 10/2012 | Kornerup et al. |
| 8,306,596 | B2 | 11/2012 | Schurman et al. |
| 8,310,415 | B2 | 11/2012 | McLaughlin et al. |

(56) References Cited

U.S. PATENT DOCUMENTS

| | | |
|---|---|---|
| 8,313,468 B2 | 11/2012 | Geipel et al. |
| 9,144,665 B2 | 9/2015 | Salstrom et al. |
| 2002/0040208 A1 | 4/2002 | Flaherty et al. |
| 2002/0095134 A1 | 7/2002 | Pettis et al. |
| 2002/0099327 A1* | 7/2002 | Wilson et al. .................. 604/43 |
| 2003/0055380 A1 | 3/2003 | Flaherty |
| 2003/0109829 A1 | 6/2003 | Mogensen et al. |
| 2003/0176852 A1 | 9/2003 | Lynch et al. |
| 2003/0199823 A1 | 10/2003 | Bobroff et al. |
| 2004/0002682 A1 | 1/2004 | Kovelman et al. |
| 2004/0010207 A1 | 1/2004 | Flaherty et al. |
| 2004/0044306 A1 | 3/2004 | Lynch et al. |
| 2004/0059316 A1 | 3/2004 | Smedegaard |
| 2004/0078028 A1 | 4/2004 | Flaherty et al. |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0116896 A1* | 6/2004 | Massengale .................. 604/506 |
| 2004/0127844 A1 | 7/2004 | Flaherty |
| 2004/0153032 A1 | 8/2004 | Garribotto et al. |
| 2004/0162521 A1 | 8/2004 | Bengtsson |
| 2004/0204673 A1 | 10/2004 | Flaherty |
| 2004/0204687 A1 | 10/2004 | Mogensen et al. |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0033237 A1* | 2/2005 | Fentress et al. ......... 604/165.03 |
| 2005/0043687 A1 | 2/2005 | Mogensen et al. |
| 2005/0065760 A1 | 3/2005 | Murtfeldt et al. |
| 2005/0090784 A1 | 4/2005 | Nielsen et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0113761 A1 | 5/2005 | Faust et al. |
| 2005/0124936 A1 | 6/2005 | Mogensen et al. |
| 2005/0137501 A1 | 6/2005 | Euteneuer et al. |
| 2005/0171512 A1 | 8/2005 | Flaherty |
| 2005/0182366 A1 | 8/2005 | Vogt et al. |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245799 A1 | 11/2005 | Brauker et al. |
| 2005/0273076 A1* | 12/2005 | Beasley et al. ............... 604/526 |
| 2005/0283144 A1 | 12/2005 | Shiono et al. |
| 2006/0001551 A1 | 1/2006 | Kraft et al. |
| 2006/0041229 A1 | 2/2006 | Garibotto et al. |
| 2006/0074381 A1 | 4/2006 | Malave et al. |
| 2006/0122577 A1 | 6/2006 | Poulsen et al. |
| 2006/0129090 A1 | 6/2006 | Moberg et al. |
| 2006/0135913 A1 | 6/2006 | Ethelfeld |
| 2006/0142698 A1 | 6/2006 | Ethelfeld |
| 2006/0173410 A1 | 8/2006 | Moberg et al. |
| 2006/0178633 A1 | 8/2006 | Garibotto et al. |
| 2006/0200073 A1 | 9/2006 | Radmer et al. |
| 2006/0263839 A1 | 11/2006 | Ward et al. |
| 2006/0264835 A1 | 11/2006 | Nielsen et al. |
| 2006/0282290 A1 | 12/2006 | Flaherty et al. |
| 2007/0016149 A1 | 1/2007 | Hunn et al. |
| 2007/0021733 A1 | 1/2007 | Hansen et al. |
| 2007/0049865 A1 | 3/2007 | Radmer et al. |
| 2007/0073229 A1 | 3/2007 | Gorman et al. |
| 2007/0073559 A1 | 3/2007 | Stangel |
| 2007/0088244 A1 | 4/2007 | Miller et al. |
| 2007/0088271 A1* | 4/2007 | Richards ....................... 604/151 |
| 2007/0093754 A1 | 4/2007 | Mogensen et al. |
| 2007/0118405 A1 | 5/2007 | Campbell et al. |
| 2007/0135681 A1 | 6/2007 | Chin et al. |
| 2007/0149925 A1 | 6/2007 | Edwards et al. |
| 2007/0191702 A1 | 8/2007 | Yodfat et al. |
| 2007/0219496 A1 | 9/2007 | Kamen et al. |
| 2008/0004515 A1 | 1/2008 | Jennewine |
| 2008/0021395 A1 | 1/2008 | Yodfat et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1 | 2/2008 | Stutz |
| 2008/0051718 A1 | 2/2008 | Kavazov et al. |
| 2008/0051727 A1 | 2/2008 | Moberg et al. |
| 2008/0051730 A1 | 2/2008 | Bikovsky |
| 2008/0051738 A1 | 2/2008 | Griffin |
| 2008/0051765 A1 | 2/2008 | Mounce |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |
| 2008/0103483 A1 | 5/2008 | Johnson et al. |
| 2008/0116647 A1 | 5/2008 | Anderson et al. |
| 2008/0119707 A1 | 5/2008 | Stafford |
| 2008/0132842 A1 | 6/2008 | Flaherty |
| 2008/0147041 A1 | 6/2008 | Kristensen |
| 2008/0160492 A1 | 7/2008 | Campbell et al. |
| 2008/0172012 A1 | 7/2008 | Hiniduma-Lokuge et al. |
| 2008/0194924 A1 | 8/2008 | Valk et al. |
| 2008/0215006 A1 | 9/2008 | Thorkild |
| 2008/0261255 A1 | 10/2008 | Tolosa et al. |
| 2008/0264261 A1 | 10/2008 | Kavazov et al. |
| 2008/0269680 A1 | 10/2008 | Ibranyan et al. |
| 2008/0269713 A1 | 10/2008 | Kavazov |
| 2008/0281297 A1 | 11/2008 | Pesach et al. |
| 2008/0294028 A1 | 11/2008 | Brown |
| 2008/0306434 A1 | 12/2008 | Dobbles et al. |
| 2008/0312608 A1 | 12/2008 | Christoffersen et al. |
| 2008/0319414 A1 | 12/2008 | Yodfat et al. |
| 2009/0005724 A1 | 1/2009 | Regittnig et al. |
| 2009/0005728 A1 | 1/2009 | Weinert et al. |
| 2009/0012472 A1 | 1/2009 | Ahm et al. |
| 2009/0062767 A1 | 3/2009 | Van Antwerp et al. |
| 2009/0076453 A1 | 3/2009 | Mejlhede et al. |
| 2009/0198191 A1 | 8/2009 | Chong et al. |
| 2009/0198215 A1 | 8/2009 | Chong et al. |
| 2009/0204077 A1 | 8/2009 | Hasted et al. |
| 2009/0221971 A1 | 9/2009 | Mejlhede et al. |
| 2009/0240240 A1 | 9/2009 | Hines et al. |
| 2009/0254041 A1 | 10/2009 | Krag et al. |
| 2009/0281497 A1 | 11/2009 | Kamen et al. |
| 2009/0326457 A1 | 12/2009 | O'Connor |
| 2010/0049129 A1 | 2/2010 | Yokoi et al. |
| 2010/0160902 A1 | 6/2010 | Aeschilimann et al. |
| 2010/0286714 A1 | 11/2010 | Gyrn et al. |
| 2010/0291588 A1 | 11/2010 | McDevitt et al. |
| 2010/0298830 A1 | 11/2010 | Browne et al. |
| 2011/0054390 A1 | 3/2011 | Searle et al. |
| 2012/0253282 A1 | 10/2012 | Nagel et al. |
| 2012/0259185 A1 | 10/2012 | Yodfat et al. |
| 2012/0265034 A1 | 10/2012 | Wisniewski et al. |
| 2012/0277554 A1 | 11/2012 | Schurman et al. |
| 2012/0277667 A1 | 11/2012 | Yodat et al. |
| 2012/0277724 A1 | 11/2012 | Larsen et al. |
| 2012/0283540 A1 | 11/2012 | Brüggemann |
| 2012/0291778 A1 | 11/2012 | Nagel et al. |
| 2012/0293328 A1 | 11/2012 | Blomquist |
| 2012/0296269 A1 | 11/2012 | Blomquist |
| 2012/0296310 A1 | 11/2012 | Blomquist |
| 2012/0296311 A1 | 11/2012 | Brauker et al. |

FOREIGN PATENT DOCUMENTS

| | | |
|---|---|---|
| EP | 2 077 128 A1 | 7/2009 |
| JP | 2002-526177 A | 8/2002 |
| JP | 2002526177 A | 8/2002 |
| JP | 2005517472 A | 6/2005 |
| JP | 2008501483 A | 1/2008 |
| JP | 2008508962 A | 3/2008 |
| WO | WO 01/93935 A1 | 12/2001 |
| WO | WO-0240083 A2 | 5/2002 |
| WO | WO 03/002018 | 1/2003 |

(56) References Cited

FOREIGN PATENT DOCUMENTS

| | | |
|---|---|---|
| WO | WO 2007/051139 | 5/2007 |
| WO | WO 2007/071255 | 6/2007 |
| WO | WO 2007/071255 A1 | 6/2007 |
| WO | WO-2007071255 A1 | 6/2007 |
| WO | WO 2009/021039 | 2/2009 |
| WO | WO 2009/021052 | 2/2009 |
| WO | WO 2009/097292 A2 | 8/2009 |
| WO | WO 2012/045667 A2 | 4/2012 |

\* cited by examiner

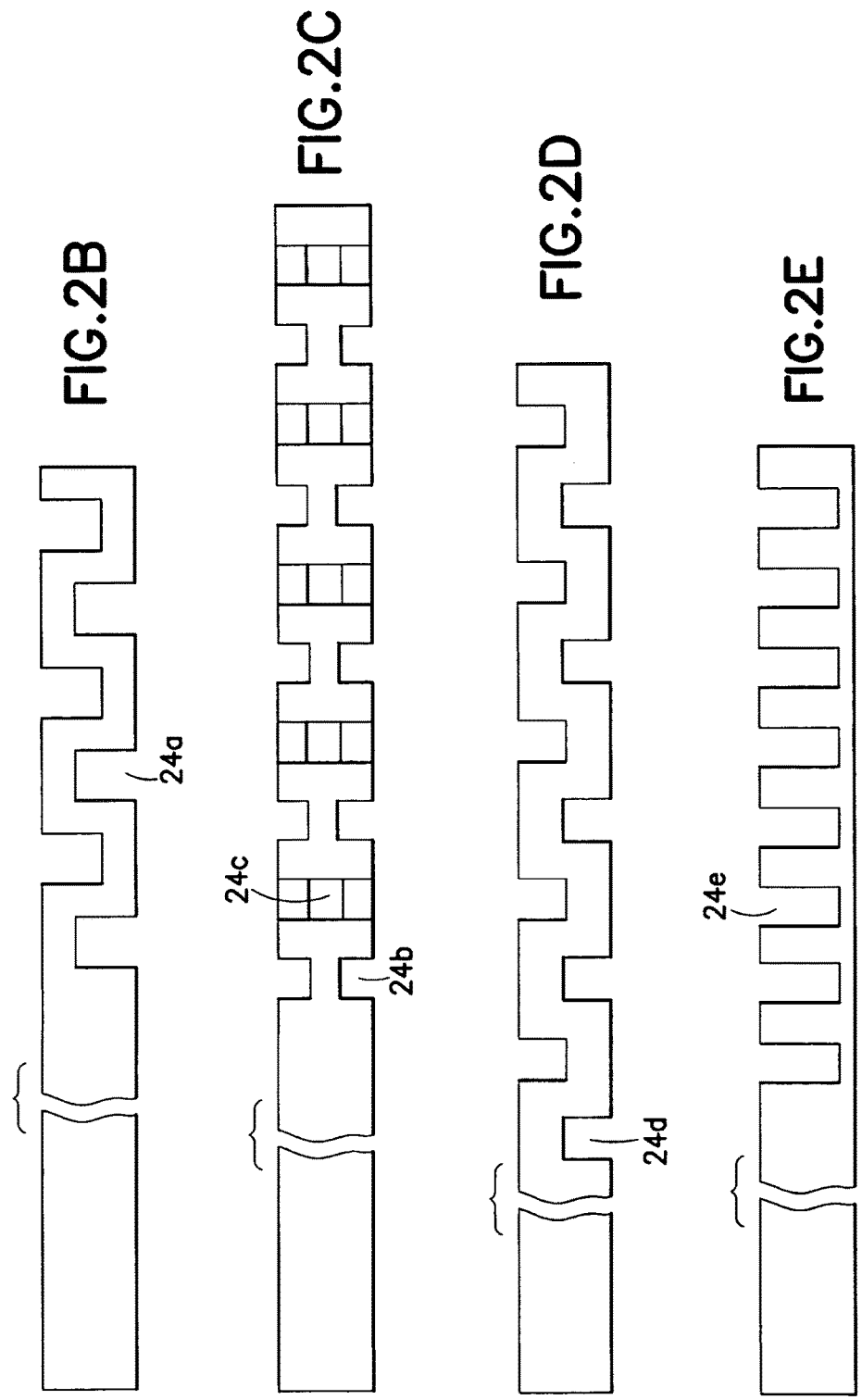

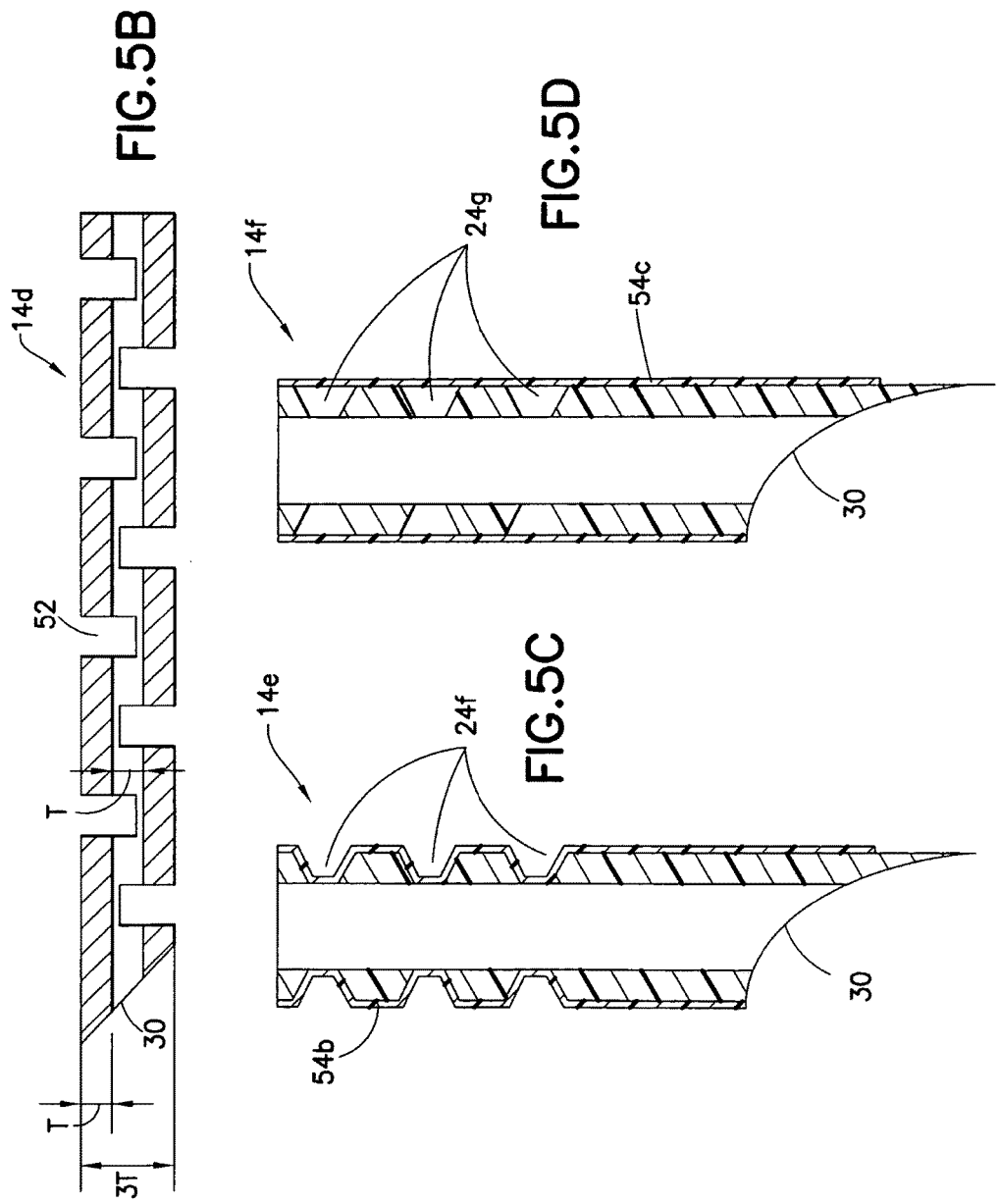

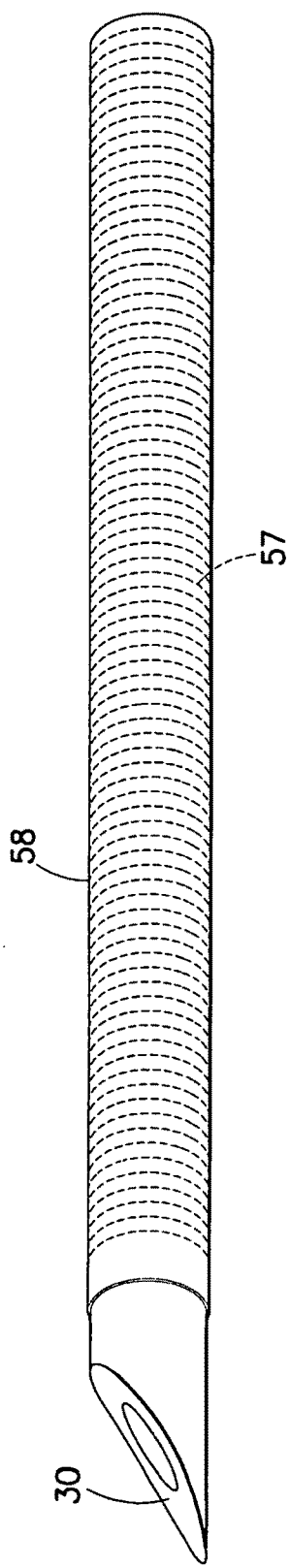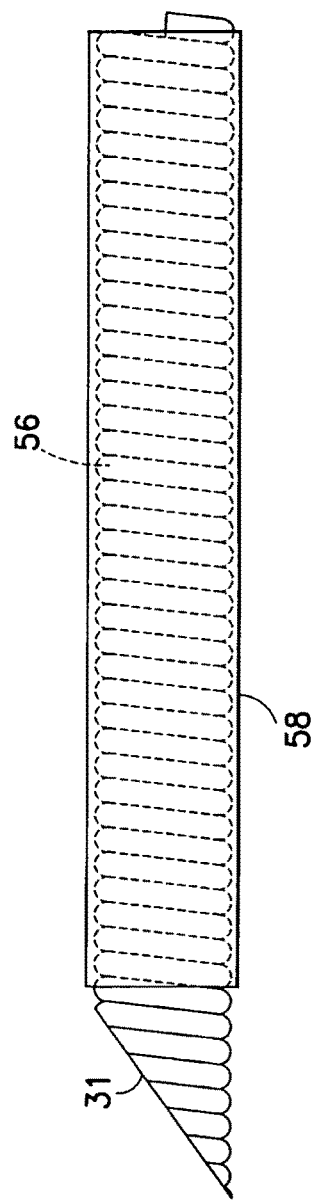
FIG.6B
FIG.6C

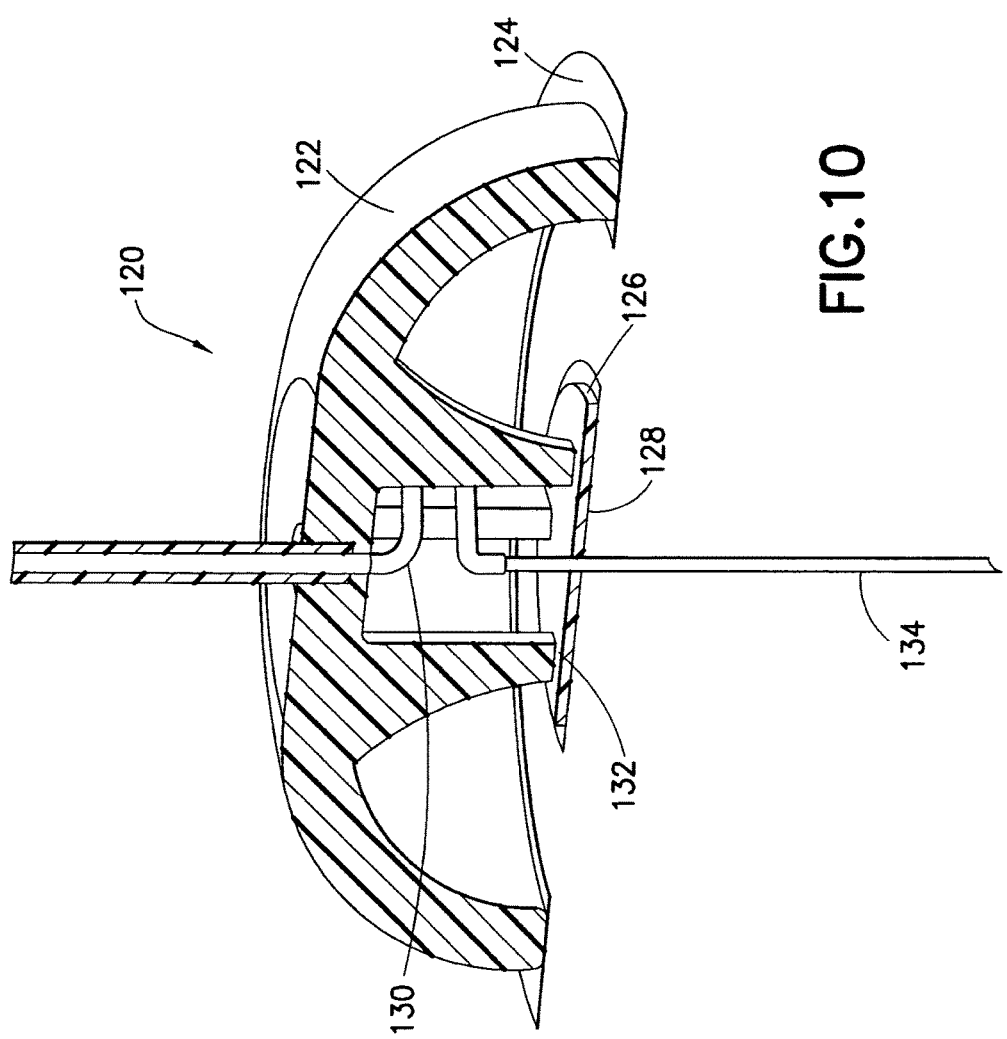

ID
INFUSION SET AND/OR PATCH PUMP HAVING AT LEAST ONE OF AN IN-DWELLING RIGID CATHETER WITH FLEXIBLE FEATURES AND/OR A FLEXIBLE CATHETER ATTACHMENT

CROSS-REFERENCE TO RELATED APPLICATIONS

This application claims the benefit under 35 U.S.C. §119(a) of U.S. Provisional Patent Application No. 61/144,072, entitled "Infusion Set And/Or Patch Pump Having At Least One Of A Rigid Catheter With Flexible Distal Tip And/Or A Flexible Catheter Attachment", filed on Jan. 12, 2009, and also claims the benefit under 35 U.S.C. §120 as a continuation-in-part of U.S. patent application Ser. No. 12/585,061, filed Sep. 2, 2009 now U.S. Pat. No. 9,375,529, entitled "Extended Use Medical Device", the entire contents, disclosure and subject matter of each of said applications being expressly incorporated herein by reference.

FIELD OF THE INVENTION

The present invention relates generally to components and elements of infusion sets and/or patch pumps, including a catheter having both rigid and flexible features desirable to users to minimize the risk of occlusion, kinking, and other undesired issues such as tissue inflammation and foreign body response, while maintaining a degree of comfort to the user.

BACKGROUND OF THE INVENTION

A large number of people, including those suffering from conditions such as diabetes use some form of infusion therapy, such as daily insulin infusions to maintain close control of their glucose levels. Currently, in the insulin infusion treatment example, there are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer blood glucose control and an improved feeling of wellness.

Recently, another type of infusion pump known as a "patch pump" has become available. Unlike a conventional infusion pump, a patch pump is an integrated device that combines most or all of the fluid components in a one-piece housing which is adhesively attached to an infusion site, and does not typically require the use of a separate infusion (tubing) set.

As patients on oral agents eventually move to insulin and their interest in intensive therapy increases, users typically look to insulin pumps for improvements in the management of their condition. Therefore, interest in better pump-related therapy is on the rise. In this and similar examples, what is needed to fully meet this increased interest are advanced, improved, and novel components and elements of current and future insulin infusion sets and/or patch pumps, including features and elements in the areas of catheter design, construction and implementation to, for example, minimize the risk of occlusion, kinking, and other undesired issues such as tissue inflammation and foreign body response, while maintaining a degree of comfort to the user.

Existing infusion set and/or patch pump catheters are manufactured of either rigid material, such as stainless steel, or soft materials, such as soft plastic, fluorinated polymers, and so forth. However, the soft plastic catheters are prone to kink or occlude with normal wear, and the rigid catheters are often found to be uncomfortable, since the rigid catheter moves around within the tissue. Both soft plastic catheters and rigid catheters can also exhibit other undesired issues such as tissue inflammation and foreign body response.

Kinking is considered to be the cessation of flow through the catheter, due to mechanical causes, such as sliding back (accordion or bellows) or folding back on the introducer needle during insertion. This failure mode could be the result of insufficient interference between the inner diameter of the catheter and the outer diameter of the introducer needle, a blunt end on the lead end of the catheter allowing excess force to be transmitted to the catheter as the catheter initially penetrates the outer surface of the skin, or excessive bounce or vibration in the insertion mechanization, again resulting in excessive force being transmitted to the catheter. Kinking can also occur during the infusion or use cycle. A typical cause of this failure is the placement of the catheter into tissue which undergoes significant movement during physical activity.

Occlusion is the cessation of flow due to biologic or pharmacologic causes, and these failures typically occur during the use cycle. Depending on the level of irritation caused by the catheter and the movement allowed by the catheter hub, the tissue can become inflamed as part of a foreign body response, resulting in reduced insulin uptake. Further, there is a tendency for insulin to crystallize when flow is reduced to a minimum (low basal flow) or temporarily stopped, e.g. for bathing, swimming or extended periods, during which time the set is disconnected. Insulin crystallization allowed to proliferate will ultimately occlude the catheter to where the required pump pressure will exceed the normal flow conditions of the pump and trigger an alarm.

Insulin infusion devices currently available on the market incorporate either a flexible polymer catheter, such as Teflon®, or a rigid catheter, such as a stainless steel cannula. In the case of the latter, the cannula has a sharp, which is used to pierce the skin, similar to an introducer needle in a conventional inserter. There are two products with in-dwelling stainless steel cannulae currently marketed for insulin infusion, the SURE-T by Medtronic and the Orbit Micro by ICU Medical. These products are recommended for individuals who have a high incidence of kinking. Unfortunately, these products are not recommended for use beyond two days, because they can occlude for the reasons mentioned above. Aside from these two products, the remaining marketed infusion sets have catheters which are manufactured from polymers, such as Teflon®.

Further, currently available patch pumps and infusion sets typically include catheters which are rigidly affixed to the hubs. This type of junction may strain the catheter and/or the tissue, such as when the skin slides atop the subcutaneous tissue. Such strain on a flexible catheter may lead to kinking, occlusion, or removal from the site. Such strain on a rigid catheter, such as a stainless steel catheter, may lead to discomfort and/or acute tissue trauma, i.e. inflammation, as the catheter moves around within the tissue.

Accordingly, a need exists for advanced, improved, and novel components and elements of current and future infusion sets and/or patch pumps, that further provide catheter design, construction and implementation to, for example, minimize the risk of occlusion, kinking, and other undesired issues such as tissue inflammation and foreign body response, while maintaining a degree of comfort to the user.

SUMMARY OF THE INVENTION

An object of the present invention is to substantially address the above and other concerns, and provide advanced, improved, and novel components and elements of current and future infusion sets and/or patch pumps, that further provide simplicity in manufacture and use improvements for both insulin and non-insulin applications.

Another object of the present invention is to provide an exemplary catheter design, construction and implementation to, for example, minimize the risk of occlusion, kinking, and other undesired issues such as tissue inflammation and foreign body response, while maintaining a degree of comfort to the user.

Another object of the present invention is to provide a hub with a fixedly attached catheter extending therefrom having a design, construction and implementation to, for example, minimize the risk of occlusion, kinking, and other undesired issues such as tissue inflammation and foreign body response, while maintaining a degree of comfort to the user.

Another object of the present invention is to provide an exemplary catheter which extends from the hub such that one or more lengths of the catheter are constructed of a rigid material.

Another object of the present invention is to provide an exemplary catheter wherein the rigid materials include one or more of a stainless steel, nitinol, titanium, rigid plastic, such as polycarbonate or TOPAS™ which is a COC, or other similar material.

Another object of the present invention is to provide an exemplary catheter having a substantially flexible length in contact with the user for use in subcutaneous (SC) infusions, intradermal (ID) infusions, intramuscular (IM) infusions, and intravenous (IV) infusions.

Another object of the present invention is to provide an exemplary catheter wherein the catheter is provided with a series and/or pattern of channels or grooves through the wall of the catheter at specific locations to allow the desired degree of flexibility.

Another object of the present invention is to provide an exemplary catheter wherein the channels or grooves are configured and arranged to optimize column strength for catheter insertion, flexibility for user comfort, and tensile strength for durability, insertion and removal.

Another object of the present invention is to provide an exemplary catheter wherein the channels or grooves are configured through the variation of channel width, channel length, bridge between channel width, width of each course between parallel channels, angle or pitch of channels, and number of courses, to achieve for example, optimized column strength for catheter insertion, flexibility for user comfort, and tensile strength for durability, insertion and removal.

Another object of the present invention is to provide an exemplary catheter wherein the channels or grooves are configured and arranged to target a desired minimum bend radius of the distal section of the catheter as well as a desired maximum arc of displacement.

Another object of the present invention is to provide an exemplary catheter wherein the channels or grooves are configured and arranged to provide additional surface area for medication delivery in subcutaneous (SC) infusions, intradermal (ID) infusions, intramuscular (IM) infusions, and intravenous (IV) infusions.

Another object of the present invention is to provide an exemplary catheter arrangement for infusion to more than one infusion site type, e.g. intradermal (ID) and subcutaneous (SC), simultaneously or each intermittently throughout the recommended use duration of the infusion device.

Another object of the present invention is to provide an exemplary catheter wherein the channels or grooves can be constructed using laser machining, electrical discharge machining (EDM), metal injection molding (MIM), plastic injection molding, chemical etching, or similar techniques.

Another object of the present invention is to provide an exemplary catheter wherein at least one portion of the catheter body is provided with a coating, such as a flexible sleeve or over-molded coating/sleeve, to provide further optimized column strength for catheter insertion, flexibility for user comfort, and tensile strength for durability, insertion and removal.

Another object of the present invention is to provide an exemplary catheter wherein the catheter tip can be beveled or sharpened to facilitate insertion through the user's skin.

Another object of the present invention is to provide an exemplary catheter wherein the catheter can be comprised as a cannula or needle with one or more of the features described above, and act as both an insertion cannula or needle, and an in-dwelling catheter.

Another object of the present invention is to provide an exemplary catheter and hub engagement wherein a flexible union is provided between the catheter and hub to enable the catheter to be embedded into the user's skin, and to move relative to the hub.

Another object of the present invention is to provide an exemplary flexible union between a catheter and hub comprising at least one of a ball-and-socket joint, a sliding plate, and a flexible bushing.

Another object of the present invention is to provide an exemplary flexible union between a catheter and hub which is sealed to allow desired movement while preventing leakage of medication through the junction.

Another object of the present invention is to provide two separate hubs as part of one infusion device, the outer hub and the catheter hub, each attached to the surface of the skin with a separate adhesive and the insulin flow between the two accomplished through a flexible fluid line or other similar connections means to isolate shock or applied forces from the surface of the outer hub to the catheter.

Another object of the present invention is to provide a polymer sleeve, such as Teflon® or Vialon®, which can be used to cover the stainless steel in-dwelling catheter and provide a bio-interface between the tissue and the needle and/or to also seal the slots in the flexible in-dwelling cannula.

Another object of the present invention is to provide a system and method for the partial withdrawal of the introducer needle or in-dwelling rigid cannula to a point where the sharp tip is not exposed to tissue and where the rigidity of the cannula can inhibit kinking.

Another object of the present invention is to configure the two hubs, which can be attached to the surface of the skin as a single device, in which the inner hub is designed to maintain the catheter position relative to the tissue in which the catheter has been inserted, and thereby reduce and eliminate irritation of the tissue and the cascade of events resulting from a foreign body response.

These and other objects are substantially achieved by providing an infusion set, patch pump, or elements thereof, having an exemplary catheter wherein one or more lengths of the catheter wall are provided with one or more channels or grooves, configured and arranged to provide a degree of catheter flexibility. The infusion set, patch pump, or elements thereof, can also have an exemplary catheter and hub comprising a flexible or rigid catheter, such as a catheter with or without channels or grooves, wherein the catheter can be retracted within a catheter sleeve. The infusion set, patch pump, or elements thereof, can also have an exemplary flexible union between the catheter and hub comprising at least one of a ball-and-socket joint, a sliding plate and a flexible bushing (including a bellows joint), a flexible tubing connection, and which is sealed to allow desired movement of the catheter while preventing leakage of medication through the junction. In doing so, a number of benefits associated with the use of rigid materials in catheter construction can be provided while, at the same time, benefits associated with the use of flexible materials in catheter construction and/or flexible engagement with the hub can also be provided, and more specifically, can be provided at targeted areas.

That is, for example, the grooves and channels, and any coatings such as a flexible sleeve or over-molded coating/sleeve thereon, and flexible unions between the catheter and hub, can be configured to optimize strength to avoid kinking, occlusion, and other undesired issues such as tissue inflammation and foreign body response, and provide flexibility for user comfort. Additional benefits of such channels, grooves and coatings can include but are not limited to providing additional surface area for medication delivery in subcutaneous (SC) infusions, intradermal (ID) infusions, intramuscular (IM) infusions, and intravenous (IV) infusions. Further, the flexible unions can increase the degrees of freedom associated with the junction of the catheter and hub.

BRIEF DESCRIPTION OF THE DRAWINGS

The various objects, advantages and novel features of the exemplary embodiments of the present invention will be more readily appreciated from the following detailed description when read in conjunction with the appended drawings, in which:

FIGS. 2A-2E are enlarged elevational views of exemplary rigid catheters having channels to provide a flexible distal tip in accordance with an embodiment of the present invention;

FIG. 5B is an enlarged cross-sectional view of the exemplary catheter of FIG. 5A;

FIG. 5C is an enlarged cross-sectional view of an exemplary catheter constructed of rigid plastic and having channels to provide flexibility in accordance with another embodiment of the present invention;

FIG. 5D is an enlarged cross-sectional view of an exemplary catheter constructed of rigid plastic and having channels to provide flexibility in accordance with another embodiment of the present invention;

FIGS. 6A-6C are enlarged perspective views of an exemplary catheter having a coiled construction to provide a flexible catheter in accordance with another embodiment of the present invention;

FIG. 10 is an enlarged cross-sectional view of an exemplary two-part hub with a flexible catheter in accordance with another embodiment of the present invention;

Throughout the drawings, like reference numerals will be understood to refer to like parts, components and structures.

DETAILED DESCRIPTION OF THE EXEMPLARY EMBODIMENTS

Figure 1:
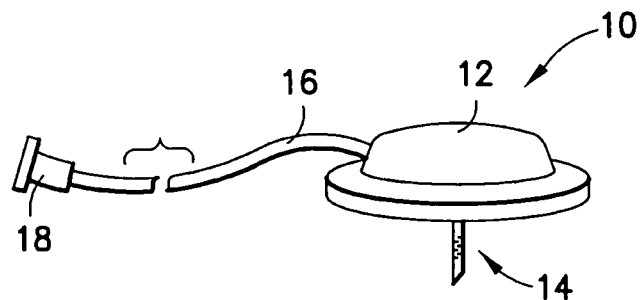
FIG. 1 is a perspective view of an infusion set which can include one or more exemplary elements in accordance with an embodiment of the present invention.

The exemplary embodiments described below address such unmet needs and illustrate a number of advanced, improved, and novel components and elements of current and future infusion sets and/or patch pumps, that further provide simplicity in manufacture and improvements in use for both insulin and non-insulin applications. For example, reducing or eliminating catheter kinking, occlusion and other undesired issues such as tissue inflammation and foreign body response, throughout the use cycle is an unmet need. Unlike the currently marketed products, the exemplary embodiments described in greater detail below are hybrids, and incorporate multiple materials, components, features, and motions in combination, to substantially reduce and eliminate the conditions that result in catheter kinking, occlusion and other undesired issues such as tissue inflammation and foreign body response. Such exemplary embodiments are presented in separate descriptions, although the individual features of these embodiments can be combined in any number of ways to meet the needs of the user.

As will be appreciated by one skilled in the art, there are numerous ways of carrying out the examples, improvements and arrangements of insulin-associated devices disclosed herein. Although reference will be made to the exemplary embodiments depicted in the drawings and the following descriptions, the embodiments disclosed herein are not meant to be exhaustive of the various alternative designs and embodiments that are encompassed by the disclosed invention.

The exemplary embodiments of the present device described below illustrate a number of features and elements in the areas of catheter design, construction and implementation to, for example, minimize the risk of occlusion, kinking, and other undesired issues such as tissue inflammation and foreign body response, while maintaining a degree of comfort to the user. A collection of exemplary elements is shown by way of the example in FIG. 1 which serves to introduce the embodiments of the present invention described in greater detail below.

FIG. 1 illustrates an exemplary infusion set 10 including the following features. As shown in FIG. 1, the exemplary infusion set 10 can comprise a hub 12, a catheter 14, a fluid line tubeset 16 and a connector 18. Additional infusion set elements and detail are omitted for clarity. Further, in an entirely self-contained patch device, the fluid line tubeset 16 and connector 18 are omitted. In the following description, a number of exemplary embodiments of a catheter 14 and catheter-hub 14/12 connection are described in greater detail, which can be provided for use with the exemplary infusion set 10 or any number of other similar devices.

As known to those skilled in the art, a catheter can comprise a polymer tube that remains in-dwelling after an introducer needle is removed, for purposes of providing fluid communication from the infusion set to the infusion site. A cannula can comprise a rigid tube, which can also remain in-dwelling. However, many of the following exemplary embodiments described below incorporate hybrids, i.e. combinations of cannulae and cannulae features, and sleeves or catheters and catheter features, and function as in-dwelling, flexible cannulae. However, to simplify the discussion, the hybrid, in-dwelling, flexible cannulae are simply described as catheters.

As noted above, one or more lengths of the catheter wall of the catheter 14 can be provided with one or more channels or grooves, and/or a coating such as a flexible sleeve or over-molded coating/sleeve, thereon, configured and arranged to provide a degree of flexibility. In doing so, a number of benefits associated with the use of rigid materials in catheter construction can be provided while at the same time, benefits associated with the use of flexible materials in catheter construction can also be provided, and more specifically, can be provided at targeted areas. That is, for example, the grooves, channels, and/or coatings, can be configured to optimize strength to avoid occlusion, kinking, and other undesired issues such as tissue inflammation and foreign body response, and provide flexibility for user comfort. If the catheter is not flexible, a greater degree of irritation and resulting inflammation can occur, causing a loss of patency or reduction in insulin uptake by the tissue at the infusion site, which will progressively degrade over time. Accordingly, the provision of a flexible catheter or catheter with a bio-interface facilitates the desired biological process in the tissue at the infusion site.

Additional benefits of such channels or grooves can include but are not limited to, providing additional surface area for medication delivery in subcutaneous (SC) infusions, intradermal (ID) infusions, intramuscular (IM) infusions, and intravenous (IV) infusions, forming a cannula or needle with one or more of the features described above, to act as both an insertion cannula or needle, and an in-dwelling catheter, and forming a multi-lumen catheter to enable infusion to one or more tissue locations or types, either simultaneously or each intermittently, e.g. intradermal (ID) tissue and subcutaneous (SC) tissue. A number of exemplary catheters will now be described individually in greater detail.

As noted above, existing infusion set catheters are manufactured of either rigid material, such as stainless steel, or soft materials, such as soft plastic, fluorinated polymers, and so forth. However, the soft plastic catheters are prone to kink and/or occlude with normal wear, and the rigid catheters are often found to be uncomfortable and are not recommended for use beyond two days, as the rigidity of the catheter causes the user to feel movement within the tissue, and also causes flow cessation, due to movement in the tissue and the ensuing inflammatory response in the tissue.

To resolve such issues associated with conventional catheter construction, design and implementation, exemplary embodiments of the present invention comprise improved and novel elements of an infusion set for the delivery, or infusion, of insulin or other medications to a user via, for example, subcutaneous (SC) infusions, intradermal (ID)

infusions, intramuscular (IM) infusions, and intravenous (IV) infusions. For example, as noted above, the infusion set 10 typically comprises the hub 12 which includes the fixedly attached catheter 14, and the tubeset 16. The tubeset 16 connects the hub 12 to an infusion pump or other insulin supply (not shown) via a connector 18. In doing so, the tubeset 16 provides for fluid communication between the infusion pump reservoir and the hub 12.

The hub 12 can be affixed to a patient's skin surface (not shown) using an adhesive (not shown) disposed on a lower surface of the hub. As shown in FIG. 1, the catheter 14 preferably protrudes from the lower surface of the hub 12 at a substantially perpendicular angle for at least a portion, although embodiments of the present invention are not limited thereto. The catheter 14 that extends from the lower surface of the hub 12 can be comprised in part, or entirely of a rigid material such as stainless steel, nitinol, titanium, or a rigid plastic such as PEEK (Polyetheretherketone), polycarbonate, TOPAS™ which is a COC, or similar materials. However, a soft plastic catheter is prone to kink and/or occlude with normal wear, and a rigid catheter is often uncomfortable.

Accordingly, in exemplary embodiments of the present invention as shown in the enlarged views of FIGS. 2A-2E, 3, 4, 5A-5D, and 6, a portion or length of the catheter 14 which is in contact with the tissue of the user is made flexible via a series or pattern of channels or grooves. The channels or grooves are designed to optimize column strength of the catheter 14 for improved catheter insertion, provide flexibility for user comfort, and further provide tensile strength for durability, insertion and removal. In exemplary embodiments, a portion of the overall catheter length can extend inside the device and for purposes of the following descriptions, the catheter is recited as the portion extending from the hub, or alternately, the length of the catheter which extends from the hub.

In the exemplary embodiments of the present invention described below, the catheter can be provided with sufficient integrity and with a sharpened, self-piercing tip 30, to allow the catheter to be implanted without the assistance of a rigid sleeve or guide, which is currently needed to pierce the tissue and resist damage to the catheter during deployment. Further, such exemplary embodiments of the present invention reduce the need for an intricate deployment mechanization, thereby reducing the overall size of the inserter and potentially allowing the inserter to become an integral part of the infusion pump.

Figure 2A:
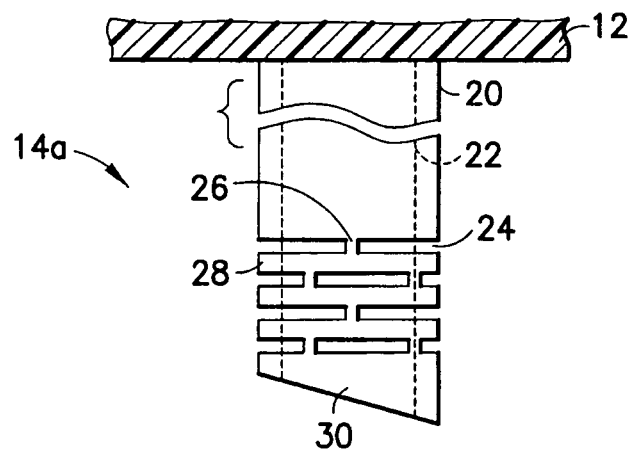

As shown in the exemplary embodiment of FIG. 2A, the catheter 14a (not shown to size) is provided with a series or pattern of channels or grooves 24. The catheter 14a of FIG. 2A comprises an outer diameter 20, an inner diameter 22, and one or more grooves 24 etched, cut, molded, or otherwise created (i.e., laser cut or chemically etched) in and/or through the catheter wall. The grooves 24 in the exemplary embodiment shown, are provided at perpendicular angles to the inner/outer surfaces, and parallel to a bottom surface of the hub 12. Each groove 24 is spaced from adjacent grooves by uncut sections 26, and spaced from adjacent parallel grooves by uncut sections 28. Further, as shown in FIG. 2A, the uncut sections 26 are staggered such that at least one or more uncut sections 26 are not adjacent.

In an exemplary embodiment of the present invention, the grooves 24 can be any suitable size, but preferably between 0.05 mm to 0.5 mm wide and 0.5 mm to 1.0 mm long, the uncut sections 26 can be between 0.05 mm to 1.0 mm long and as wide as the grooves 24, and the uncut sections 28 between grooves 24 can be between 0.05 mm to 1.0 mm. The channels or grooves are designed to provide flexibility in one, two, or more axis, and optimize column strength of the catheter for improved catheter insertion, hoop strength of the catheter to prevent collapse or kinking once implanted, provide flexibility for user comfort, and further provide tensile strength for durability, insertion and withdrawal.

In the embodiment shown in FIG. 2A, the series or pattern of channels 24 are located near the end of the catheter 14a. That is, the portion of the catheter 14a closest to the hub 12 remains intact, and the series or pattern of channels 24 are provided near an opposite end of the catheter 14a. The series or pattern of channels 24 are ended at a point near a sharpened, self-piercing tip 30, which can be beveled or sharpened to facilitate insertion through the patient's skin. An exemplary embodiment of such a sharpened, self-piercing tip 30 is shown in greater detail in FIGS. 5A, 5B and 6, described in greater detail below. As shown in greater detail in FIGS. 5A, 5B and 6, the sharpened, self-piercing tip 30 can comprise a radius cut to create a beveled tip. Where the catheter is provided with such a sharpened, self-piercing tip to allow the insertion, the catheter can act also as the insertion needle, thereby further reducing the complexity of the insertion step.

Where the series or pattern of channels are positioned in a manner suitable to do so, such channels can also be used for targeted fluid communication. However, where not positioned to do so, one or more of the channels can be sealed with a biointerface sheath or coating such as a flexible sleeve or over-molded coating/sleeve, as described in greater detail below.

In this or any other exemplary embodiment described below, the series or pattern of channels can be provided near one or both opposite ends of the catheter, or at any portion therebetween, or any combination of each. In still other exemplary embodiments, the substantial entirety of the catheter body can be provided with such series or pattern of channels. The exemplary embodiments shown are for illustrative purposes only, and are not intended to limit the present invention to a specific distribution area of the series or pattern of channels.

In an exemplary embodiment of the present invention, the catheter 14a can be any suitable size, but preferably between 3.5 mm to 12 mm long, with an inner diameter 22 of between 0.20 mm to 0.78 mm and outer diameter 20 of between 0.25 mm to 0.8 mm. The first groove 24 at the distal end of the catheter 14a can be provided between 0.5 mm and 2.0 mm from the distal end of the catheter, and the last groove can be provided between 2.5 mm to 3.0 mm from the base 12. In doing so, a length of catheter 14a between 1.5 mm and 9.0 mm long is provided with the channels 24. In some cases, where the first groove may interfere with the back angle of the sharp, the first groove may be provided at a greater distance from the distal end of the catheter. The channels or grooves are designed to provide flexibility in one, two, or more axis, and optimize column strength of the catheter for improved catheter insertion, strength of the catheter to prevent collapse or occlusion once implanted, provide flexibility for user comfort, and further provide tensile strength for durability.

In the exemplary embodiment shown in FIG. 2A, each of the channels 24 are provided at perpendicular angles to the inner/outer surfaces, and parallel to a bottom surface of the hub 12. However, in this and other exemplary embodiments of the present invention, the channels can be provided at non-perpendicular angles.

A number of other exemplary embodiments of the present invention comprising channels provided at perpendicular angles to the inner/outer surfaces, and parallel to a bottom surface of the hub are shown in FIGS. 2B-2E. As shown in FIG. 2B, the catheter can have alternating "upper" and "lower" channels 24a.

In the exemplary embodiment shown in FIG. 2C, the catheter is shown having opposite "upper" and "lower" channels 24b, and opposite "front" and "rear" channels 24c (i.e., rotated 90 degrees from the upper and lower channels). The dimensions of the channels 24b and 24c are similar to those of FIG. 2B. In the exemplary embodiment shown in FIG. 2D, the catheter is shown having opposite "upper" and "lower" channels 24d, but of lesser depth than those of FIG. 2B (i.e, the channels cross the center-line in the embodiment of FIG. 2B to allow flexibility in all directions, wherein the channels stop short or at the center-line in the embodiment of FIG. 2D). In the exemplary embodiment shown in FIG. 2E, the catheter is shown having only "upper" channels 24e, and of greater depth than those of FIGS. 2B, 2C and 2D. In such embodiments, the width, depth, and other placement features of the channels can be used as a factor to permit degrees and direction of flexibility.

Figure 3:
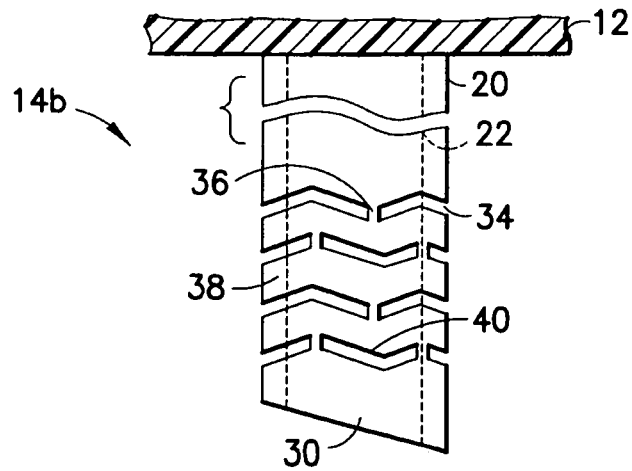
FIG. 3 is an enlarged elevational view of an exemplary rigid catheter having channels to provide a flexible distal tip in accordance with another embodiment of the present invention.

As shown in the exemplary embodiment of FIG. 3, the catheter 14b (not shown to size) can also be provided with a series or pattern of channel or grooves 34 which are configured in a saw-tooth pattern. The catheter 14b of FIG. 3 comprises the outer diameter 20, the inner diameter 22, and one or more grooves 34 etched, cut, molded, or otherwise created in and/or through the catheter wall. The grooves 34 in the exemplary embodiment shown, are provided in a saw-tooth pattern relative to the inner/outer surfaces, and to a bottom surface of the hub 12. Each groove 34 is spaced from adjacent grooves by uncut sections 36, and spaced from adjacent grooves by uncut sections 38. In an exemplary embodiment, an angle 40 of between 10 degrees and 45 degrees can be used, but the invention is not limited thereto. For example, in yet other embodiments of the present invention, the grooves 34 can be provided in a substantially sinusoidal pattern. Further, as shown in FIG. 3, the uncut sections 36 can be staggered such that at least one or more uncut sections 36 are not adjacent.

In an exemplary embodiment of the present invention, the grooves 34 can be any suitable size, but preferably between 0.05 mm and 0.5 mm wide and 0.5 mm to 1.0 mm long, the uncut sections 36 can be between 0.05 mm to 1.0 mm long and as wide as the grooves 34, and the uncut sections 38 between grooves 34 can be between 0.05 mm to 1.0 mm.

In the exemplary embodiment shown in FIG. 3, the series or pattern of channels 34 are also located near the end of the catheter 14b. That is, the portion of the catheter 14b closest to the hub 12 remains intact, and the series or pattern of channels 34 are provided near an opposite end of the catheter 14b. The series or pattern of channels 34 are ended at a point near a sharpened, self-piercing tip 30, which can be beveled or sharpened to facilitate insertion through the patient's skin.

In an exemplary embodiment of the present invention, the catheter 14b can be any suitable size, but preferably between 3.5 mm to 12 mm long, with an inner diameter 22 of between 0.20 mm to 0.78 mm and outer diameter 20 of between 0.25 mm to 0.8 mm. The first groove 34 at the distal end of the catheter 14b can be provided between 0.5 mm and 2.0 mm from the distal end of the catheter, and the last groove can be provided between 2.5 mm to 3.0 mm from the base 12. In doing so, a length of catheter 14b between 1.5 mm and 9.0 mm long is provided with the channels 34. In some cases, where the first groove may interfere with the back angle of the sharp, the first groove may be provided at a greater distance from the distal end of the catheter.

In the exemplary embodiment shown, the catheter provides a means (i.e., cross-porting) for transferring drug to the infusion site tissue, and therefore the slots do not extend all the way back to the proximal end of the catheter. This distance, approximately 3 mm, is intended to position the cross-ports into the SC tissue, and inhibit drug flow to the intra-dermal (ID) tissue. For the concepts shown in images 2B, 2C, 2D, 2E, 5A, 5B, 5C, 5D, 6, 10, 11, 12A, 12B, 13A, 13B, and 14 the catheter has been rendered flexible from a distance starting just behind the bevel of the tip and extending into the infusion set hub to allow the flexible catheter to "snake" from the flat plane or axis of the hub to enter and extend into the tissue perpendicular to that axis.

Figure 4:
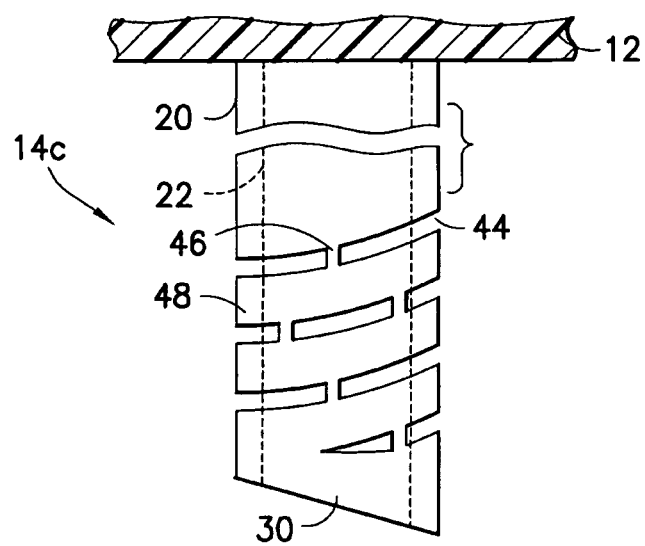
FIG. 4 is an enlarged elevational view of an exemplary rigid catheter having channels to provide a flexible distal tip in accordance with yet another embodiment of the present invention.

As shown in the exemplary embodiment of FIG. 4, the catheter 14c can also be provided with a series or pattern of channels or grooves 44 which are configured in a helix pattern oriented about a center axis of the catheter. A helix is a three-dimensional coil that runs along the surface of a cylinder, in this case, the body of the catheter. The catheter 14c of FIG. 4 comprises the outer diameter 20, the inner diameter 22, and one or more grooves 44 etched, cut, molded, or otherwise created in and/or through the catheter wall. The grooves 44 in the exemplary embodiment shown, are provided in a helix pattern relative to the inner/outer surfaces, and to a bottom surface of the hub 12, and oriented about a center axis of the catheter. Each groove 44 is spaced from adjacent grooves by uncut sections 46, and spaced from adjacent grooves by uncut sections 48. Further, as shown in FIG. 4, the uncut sections 46 are staggered such that at least one or more uncut sections 46 are not adjacent.

In an exemplary embodiment of the present invention, the grooves 44 can be any suitable size, but preferably between 0.05 mm and 0.5 mm wide and 0.5 mm to 1.0 mm long, the uncut sections 46 can be between 0.05 mm to 1.0 mm long and as wide as the grooves 44, and the uncut sections 48 between grooves 44 can be between 0.05 mm to 1.0 mm.

In the embodiment shown in FIG. 4, the series or pattern of channels 44 are also located near the end of the catheter 14c. That is, the portion of the catheter 14c closest to the hub 12 remains intact, and the series or pattern of channels 44 are provided near an opposite end of the catheter 14c. The series or pattern of channels 44 are ended at a point near a sharpened, self-piercing tip 30, which can be beveled or sharpened to facilitate insertion through the patient's skin.

In an exemplary embodiment of the present invention, the catheter 14c can be any suitable size, but preferably between 3.5 mm to 12 mm long, with an inner diameter 22 of between 0.20 mm to 0.78 mm and outer diameter 20 of between 0.25 mm to 0.8 mm. The first groove 44 at the distal end of the catheter 14c can be provided between 0.5 mm and 2.0 mm from the distal end of the catheter, and the last groove can be provided between 2.5 mm to 3.0 mm from the base 12. In doing so, a length of catheter 14c between 1.5 mm and 9.0 mm long is provided with the channels 44. In some cases, where the first groove may interfere with the back angle of the sharp, the first groove may be provided at a greater distance from the distal end of the catheter.

As noted above, in still other exemplary embodiments, the substantial entirety of the catheter body between distal and proximal ends can be provided with such series or pattern of channels. In this case, the series or pattern of channels may not be positioned for fluid communication and therefore, one or more of the channels can be sealed with a biointerface sheath or coating such as a flexible sleeve or over-molded coating/sleeve, as described in greater detail below.

Figure 5A:
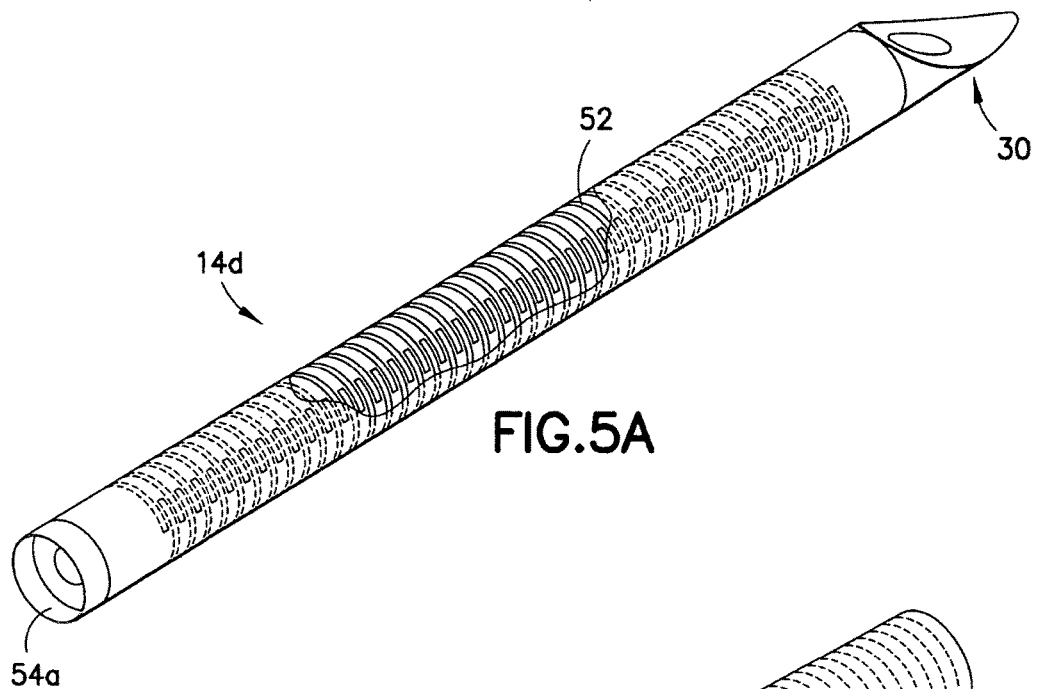
FIG. 5A is an enlarged perspective view of an exemplary catheter having channels to provide a flexible catheter in accordance with another embodiment of the present invention.

Through the use of the exemplary embodiments described above, a device can be configured to provide a cannula or needle with one or more of the features described above, to act as both an insertion cannula or needle, and an in-dwelling catheter. One such exemplary embodiment is shown in FIGS. 5A and 5B, and preferably comprises a rigid catheter 14d (for example, stainless steel), with a sharpened, self-piercing tip 30 and alternating, parallel slots 52, etched, cut, molded, or otherwise created (i.e., laser cut or chemically etched) in and/or through the catheter wall, along the substantially entire shaft of the catheter. The slots 52 can be provided substantially as described above in regard to the exemplary embodiment of FIGS. 2A-2E, wherein spacing between slots 52 can be configured to provide the slight overlap of the slot ends as shown, or as described above in regard to the exemplary embodiment of FIGS. 3 and 4. However, as the exemplary embodiments of the present invention are described in regard to catheter gauges of 24 to 34 gauges, at extreme values, the above numerical dimensions can result in a slot/spacing relationship that can change. For example, for a 34 gauge catheter, the shortest length slot, i.e., 0.5 mm long, would only allow one attachment point around the diameter, which could limit design alternatives and device performance.

Accordingly, as illustrated in FIG. 5B, the catheter of extreme values, or any value therebetween, can be designed to have a wall thickness of T (i.e., with an outside diameter of approximately 3T, and an inside diameter of approximately T). In doing so, each of channels 52 can be between 1T to 6T wide, and preferably between 2T and 3T. The uncut spaces between channels can be between 1T and 6T, and preferably between 2T and 3T.

In the embodiment of FIGS. 5A and 5B, the alternating slots 52 enable the catheter 14d to flex, yet provide a rigidity or column strength necessary for insertion into the user's skin, but flex to provide a comfortable in-dwelling catheter. The exemplary stainless steel catheter 14d is preferably a unitary body having a sharpened, self-piercing tip 30 at the distal end. As shown in FIG. 5A, the sharpened, self-piercing tip 30 can comprise a radius cut to create a beveled tip. Where the catheter is provided with such a sharpened, self-piercing tip to allow the insertion, the catheter can act as the insertion needle, thereby further reducing the complexity of the insertion step.

Further, as shown by the exposed illustrative portion of FIG. 5A, the catheter 14d can be sheathed or coated over some desired portion by a coating, such as Vialon® or Teflon®, to create a sleeve 54a that provides a biocompatible outer fluid seal for enabling a drug fluid to enter to the user through the tip of the catheter, provide a seal so that leakage does not occur through the slots 52, and/or provide a cover into which the insertion cannula or in-dwelling catheter can be slightly retracted to cover the sharpened end thereof.

The outer sheath or sleeve 54a can be processed to the appropriate inner diameter and pulled over the catheter 14d for attachment. Depending on the specific sheath or sleeve material, the attachment may be facilitated by a dip coating process, heat shrinking, bonding, or any other suitable process. The outer sheath or sleeve 54a can comprise a polymer sleeve, such as Teflon® or Vialon®, which can be used to cover the stainless steel in-dwelling catheter and provide a bio-interface between the tissue and the needle and/or to also seal the slots in the flexible in-dwelling cannula. Additional disclosure of the exemplary Vialon® material can be found in commonly assigned U.S. Pat. No. 5,226,899 and U.S. Pat. No. 5,453,099 of Min-Shiu Lee et al., U.S. Pat. No. 5,545,708 of Theo Onwunaka et al., and U.S. patent application Ser. No. 12/585,061 of Gary Searle et al., the entire contents, disclosure and subject matter of each being expressly incorporated herein by reference. In yet other exemplary embodiments of the present invention, any suitable fluid tight material could be used to form the sheath or coating such as the flexible sleeve or over-molded coating/sleeve. In this or other exemplary embodiments of the present invention, a material which can become softer and/or more flexible once inserted can also be used.

Such polymers, overmolding, and other construction techniques and materials can be used in the construction of the in-dwelling cannula or catheter. For example, FIGS. 5C and 5D are enlarged cross-sectional views of a portion of exemplary catheters constructed of rigid plastic and having channels to provide flexibility in accordance with embodiments of the present invention.

In FIG. 5C, an exemplary catheter 14e is shown constructed of injection molded rigid plastic, wherein the slots 24f provide flexibility. As the catheter 14e is injection molded, the slots 24f, needle point, and all other finished features can be molded in any configuration desired such that no secondary operations would be required. Further, as with the embodiment shown in FIG. 5A, an over-molded outer sheath or sleeve 54b can comprise a polymer, such as Teflon® or Vialon®, and be used to cover the catheter, provide a bio-interface between the tissue and the catheter, and/or seal the slots in the catheter.

A similar exemplary embodiment is shown in FIG. 5D in which an exemplary catheter 14f is shown constructed of injection molded rigid plastic, wherein the slots 24g provide flexibility. As the catheter 14f is again injection molded, the slots 24g, needle point, and all other finished features can be molded in any configuration desired such that no secondary operations would be required. Further, an extruded outer sheath or sleeve 54c can comprise a polymer sleeve, such as Teflon® or Vialon®, and be used to cover the catheter, provide a bio-interface between the tissue and the catheter, and/or seal the slots in the catheter. In the exemplary embodiments, the outer sleeve can be over-molded as part of a 2-shot molding process, or can be extruded separately and assembled to the insertion cannula or in-dwelling catheter.

Figure 6A:
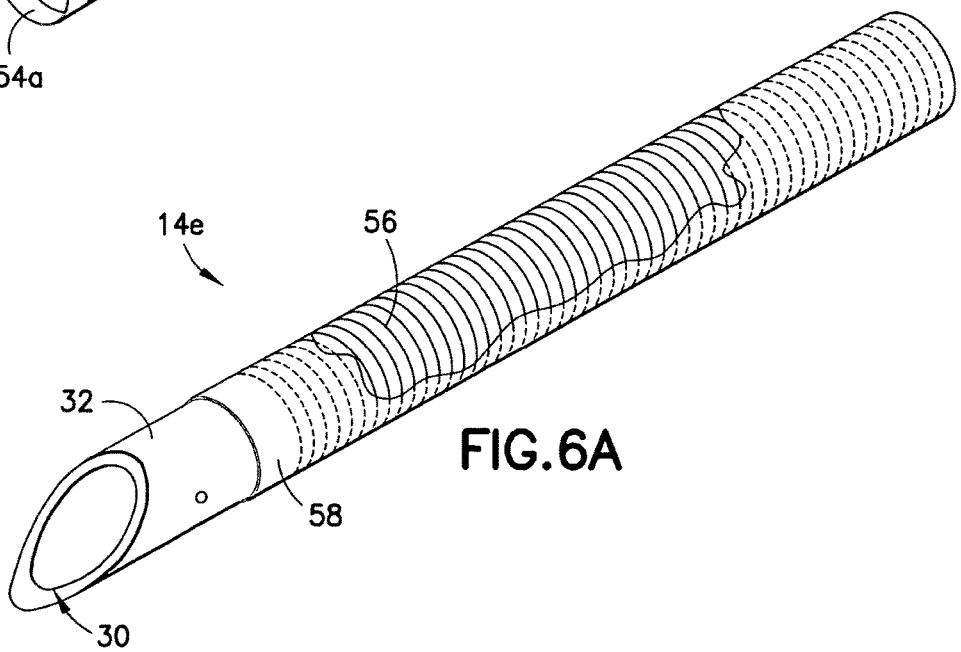

Still another exemplary embodiment wherein the substantially entire catheter body can be provided with such series or pattern of channels is shown in FIG. 6A, and preferably comprises a catheter 14g with a sharpened rigid, such as stainless steel, needle tip 32, attached to a torsion spring 56. The needle tip 32 and sharpened, self-piercing tip 30 thereof, enables penetration into the user's skin and is preferably welded to the torsion spring 56, but may be attached using any suitable method.

The torsion spring 56 provides similar benefits as the embodiments described above in that it provides column strength for insertion, flexibility for user comfort, and tensile strength for durability. Such a torsion spring 56 can be sheathed or coated over some desired portion by a coating such as a flexible sleeve or over-molded coating/sleeve material, such as a Vialon® or Teflon® sleeve 58 for sealing the communicated fluid within the inner cavity of the torsion spring.

In another exemplary embodiment shown in FIG. 6B, the torsion spring 57 can also be laser cut or chemically etched from the proximal portion of the solid steel cannula, i.e. behind the sharp tip 30, by lasing a continuous spiral or helix. In this case, the proximal end could either be opened or closed (i.e., open to deliver contents, or closed to urge content delivery through other openings). In doing so, the one-piece spiral or helix cut structure enables the shaft to be flexible, the column strength to be maintained which enables insertion, and allows hoop strength to be maintained which prevents collapse of the inner lumen. As with the embodiments described above, the torsion spring 57 can be sheathed or coated over some desired portion by a coating such as a flexible sleeve or over-molded coating/sleeve material, such as a Vialon® or Teflon® sleeve 58 for sealing the communicated fluid within the inner cavity of the torsion spring.

In another exemplary embodiment shown in FIG. 6C, the torsion spring 56 can be manufactured from a continuous length of torsion spring, and then lasing a continuous weld to connect a number of coils at the end of the spring, and then grinding the welded end to create the bevel end 31. As with the embodiments described above, the torsion spring 57 can be sheathed or coated over some desired portion by a coating such as a flexible sleeve or over-molded coating/sleeve material, such as a Vialon® or Teflon® sleeve 58 for sealing the communicated fluid within the inner cavity of the torsion spring.

The exemplary catheters described above can be provided with any suitable wire or spring cross section, inner diameter, and outer diameter, and may alternatively comprise a rectangular cross-section to maximize the internal diameter, as would be appreciated by one of ordinary skill in the art. Additionally, the ends of each do not need to comprise an opening for the flow of drug to the user. It may desirable to implement an embodiment with a closed end, and having side ports located near the tip or elsewhere for enabling the flow of drug to the user. An exemplary catheter having a plurality of holes at or near a tapered tip, and a method of constructing and using such a catheter is described in U.S. patent application Ser. No. 12/427,633, filed Apr. 21, 2009, entitled "Systems And Methods For Improving Catheter Hole Array Efficiency", the entire contents, disclosure and subject matter of which being expressly incorporated herein by reference. In other exemplary embodiments, a flexible catheter can be coupled with a sharpened tip optionally hardened relative to the catheter for entering the user's skin.

An additional feature to be used in any of the above embodiments provides a means for heparinizing the catheter. Heparinization of the catheter may be performed prior to initial insertion into the user's skin or during the variable insertion and retraction motions. Heparinization may be performed by coating the catheter with heparin by any method available to one of ordinary skill in the art. A heparinized catheter may facilitate preservation of the infusion site by preventing blood coagulation at the infusion site which may block or otherwise complicate the infusion site. The drug Heparin is one in a family of anti-coagulants and one of ordinary skill in the art would appreciate that similar drugs can be substituted to achieve the same benefits without departing from the scope and spirit of embodiments of the present invention.

By providing a distal portion or length of the catheter which is in contact with the tissue of the user with the channels, a portion or length of the catheter is made flexible, while maintaining a rigid portion or length of the catheter. The channels or grooves are designed to optimize column strength of the catheter for improved catheter insertion, provide flexibility for user comfort, and further provide tensile strength for durability.

In the construction, design and implementation of the catheter described above, the width of each channel, the length of each channel, width of each bridge or uncut sections between channels, width of uncut sections between parallel channels, angle or pitch of channels relative to the axis of the catheter, and the number of courses, can be determined to provide a desired minimum bend radius of the distal section of the catheter axis, and the maximum arc of displacement. The channels or grooves can be configured to pass entirely through the thickness of the catheter, or can be configured to pass through one wall of the catheter, that is, entirely between the outer and inner surfaces or some portion thereof. In these and other embodiments of the present invention, a combination of any of the above configured grooves or channels can be provided as desired. That is, one or more of the grooves or channels illustrated in FIGS. 2-6, including the coatings or sheaths, can be provided in a single catheter.

Further, as noted above, the presence of the channels or grooves at the distal section of the catheter also allows additional surface area for medication delivery to the tissue of the user. That is, when a substance is delivered to a targeted area via the catheter, some delivery occurs via the provided grooves or channels when desirable to do so. In other exemplary embodiments, the catheter can be sheathed or coated over some desired portion by a coating, such as Vialon® or Teflon®, to create a sleeve that provides a biocompatible outer fluid seal for enabling a drug fluid to enter to the user through the tip of the catheter, and provide a seal so that leakage doesn't occur through the slots.

Still further, in each embodiment of the present invention, the channels or grooves can be constructed using laser machining, electrical discharge machining (EDM), metal injection molding (MIM), plastic injection molding, chemical etching, or similar techniques, such that the channels or grooves are cleanly cut through the wall of the catheter without creating obstacles, undesired edges, or dead spaces.

If required, the catheter can be reworked (i.e. a secondary operation) after the process used to induce flexibility, e.g. laser cutting, EDM, chemical etch, etc. For example, electropolishing can be used to remove surface imperfections, and create an oxide layer for improved biocompatibility and corrosion resistance. Passivation can be used with stainless steel and catheters produced from other metals with some amount of ferrous composition, e.g. nitinol, to remove iron contamination from the surface. Microblasting can also be used to establish a clean, textured surface for over-molding.

Further, where the catheter is provided with both flexible and rigid features, and the sharpened, self-piercing tip, thereby allowing the insertion of the catheter without the use of an insertion needle, the catheter can act as the insertion needle and can remain in-dwelling, thereby further reducing the complexity of the insertion step. Such a catheter can be sheathed or coated over some desired portion by a coating such as a flexible sleeve or over-molded coating/sleeve material, such as a Vialon® or Teflon® sleeve.

In the above described and other exemplary embodiments of the present invention, further benefit can be achieved by providing a flexible union between the catheter and the hub. Currently available patch pumps and infusion sets typically include catheters which are rigidly affixed to the hubs. This type of junction may strain the catheter and/or the tissue, such as when the skin slides atop the subcutaneous tissue. Such strain on a flexible catheter may lead to kinking, occlusion, or removal from the site. Such strain on a rigid catheter, such as a stainless steel catheter, may lead to discomfort and/or acute tissue trauma as the catheter moves around within the tissue.

Accordingly, exemplary embodiments of the present invention are further provided to enable the hub to move with the skin while minimizing any effect of such movement on the catheter and the insertion site. Examples of such a flexible union can be provided by, but are not limited to, a ball-and-socket joint, a sliding plate junction, a separate inner hub with a separate adhesive attachment a flexible tubing connection, and a flexible bushing junction (including a bellows connection or bellows joint), provided between the catheter and the hub or patch pump.

Still further embodiments of the present invention can comprise two or more separate hubs as part of one infusion device, such as the outer hub and the catheter hub, each attached to the surface of the skin with a separate adhesive and wherein the flow between the two is preferably accomplished through a flexible fluid line or other similar connections means to isolate shock or applied forces from the surface of the outer hub to the catheter. The two hubs, which can be attached to the surface of the skin as a single device, can be further configured such that the inner hub maintains the catheter position relative to the tissue in which the catheter has been inserted, and thereby reduce and eliminate irritation of the tissue and the cascade of events resulting from a foreign body response.

Figure 7:
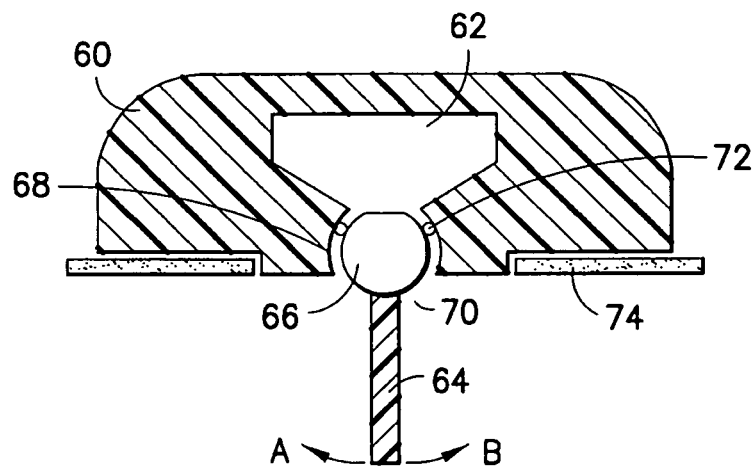
FIG. 7 is an enlarged cross-sectional view of an exemplary catheter and hub flexible union engagement comprising a ball-and-socket joint to provide a flexible connection in accordance with yet another embodiment of the present invention.

FIG. 7 is an enlarged cross-sectional view of a hub, such as provided with a patch pump, incorporating one such exemplary catheter and hub engagement comprising a ball-and-socket joint in accordance with an embodiment of the present invention. In FIG. 7, a hub 60 is shown having a fluid, medication or other content storing reservoir 62 positioned above or in fluid communication with a catheter 64. A ball joint 66 can be secured or otherwise formed at one end of the catheter 64, and is provided to rotatably secure the catheter 64 with the lower surface of the hub 60.

Specifically, a lower portion of the hub 60 body can comprise a circular detent opening 68 or other similar opening into which the ball joint 66 of the catheter 64 can be captured. The circular detent opening 68 can be sized to allow the ball joint 66 to be press-fit into and thereafter captured by the circular detent opening 68.

The ball joint 66 may also be captured within the circular detent opening 68 by manipulating one or more elements of the hub 60 to allow expansion and contraction of the detent opening 68 to facilitate installation and thereafter capture of the ball joint 66 within the detent opening 68, or the ball joint 66 may be captured within the detent opening 68 during the assembly of the body of the hub 60. In doing so, the catheter 64 is free to rotatably move relative to the hub 60 in a number of directions, such as those illustrated by the directions of arrows A and B. That is, the catheter 64 of FIG. 7 is free to rotate to the extent permitted by a bottom opening 70 of the detent opening 68 in the lower surface of the body of the hub 60.

The catheter 64 can comprise any suitable catheter, such as those described above, and the ball joint 66 can be formed of a material identical or similar to that of the catheter 64, and can comprise an opening therethrough to allow uninterrupted fluid communication during rotation and at each rotated position of the catheter 64 and ball joint 66.

Further, the junction between the catheter 64 and the hub 60 can be sealed to prevent leakage either from the chamber 62 or into the chamber 62, by one or more sealing elements 72. The sealing element 72 can comprise any number of suitable elements, such as one or more O-rings, bushings, washers, molded elements or similar sealing elements. The sealing element 72 can be further configured to control the rotatable movement of the catheter 64 by providing a degree of friction between the ball joint 66 of the catheter 64 and the hub 60. The hub 60 can further comprise additional elements, such as the adhesive layer 74 to secure the hub 60 to a skin surface for use, and still other elements which are omitted from the illustration of FIG. 7 for clarity.

In an exemplary embodiment of the present invention, the ball joint 66 can comprise a substantially circular element having a diameter of any suitable size, but preferably between 0.5 mm to 4.0 mm. Accordingly, the detent opening 68 can have a diameter between 0.5 mm to 5.0 mm, and the bottom opening 70 of the detent opening can have a diameter between 0.4 mm to 3.8 mm wide. In embodiments of the present invention, the bottom opening 70 can be circular, oval, or any shape desired to provide the needed degrees of movement.

In yet other embodiments of the present invention, a sliding plate can be provided to allow movement between the catheter and hub, and/or a flexible bushing can be provided to allow movement between the catheter and hub. Although degrees of movement are provided by each of the ball-and-socket, sliding plate, and flexible bushing, subtle differences in the movement provided by each (i.e., rotational, slidable, or combinations thereof) can result in a preference for one exemplary embodiment in a specific application.

Figure 8:
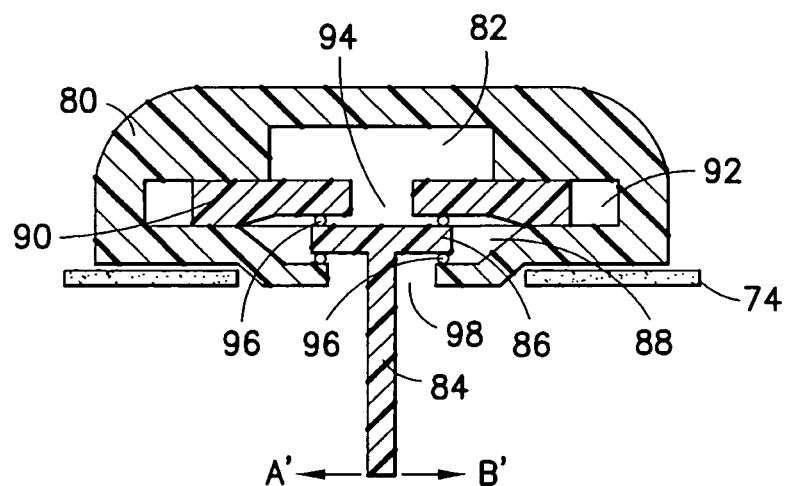
FIG. 8 is an enlarged cross-sectional view of an exemplary catheter and hub flexible union engagement comprising a sliding plate junction to provide a flexible connection in accordance with yet another embodiment of the present invention.

For example, FIG. 8 is an enlarged cross-sectional view of a hub, such as provided with a patch pump, incorporating an exemplary catheter and hub engagement comprising such a sliding plate junction in accordance with another embodiment of the present invention. In FIG. 8, a hub 80 is shown having a fluid, medication or other content storing reservoir 82 positioned above or in fluid communication with a catheter 84. The catheter 84 comprises an element at one end, such as the planar element 86, which is slidably captured in an opening 88 to slidably secure the catheter 84 with the lower surface of the hub 80.

Specifically, a lower portion of the hub body can comprise the opening 88, formed between a lower surface of the chamber 82 and one or more elements 90 captured in one or more notches 92, into which the planar element 86 can be captured. In an exemplary embodiment of the present invention, the notch 92 is formed in an inner wall of the reservoir 82 and encircles the entire circumference of the reservoir. Accordingly, the element 90 can comprise a substantially circular washer-shaped member which can be assembled into the notch 92. A thickened portion of the element 90 can be provided to secure the element 90 into the notch 92. A narrower portion of the element 90 can be provided near a central opening 94 to allow a degree of deflection to assist in holding the planar member 86 and sealing elements 96 described in greater detail below.

The planar element 86 can be captured within the opening 88 through the assembly of the hub body or in a similar manner. In doing so, the catheter 84 is free to move relative to the hub 80 in a number of directions, such as those illustrated by the directions of arrows A' and B'. That is, the catheter 84 of FIG. 8 is free to slide to the extent permitted by the bottom opening 98 in the lower surface of the hub 80, and/or as permitted by the travel of the planar member 86 within the opening 88. Some rotational movement of the catheter 84 relative to the hub 80 can also be provided as permitted by the deflection of the element 90 by the planar member 86 (see for example, the arrows A and B of FIG. 7).

The catheter 84 can comprise any suitable catheter, such as those described above. The planar member 86 can be formed of a material identical or similar to that of the catheter 84, and can comprise an opening therethrough to allow uninterrupted fluid communication during sliding and at each position. The securing element 90 can also be formed of a material identical or similar to that of the planar member 86, the hub 80, or any other suitable material.

Further, the junction between the catheter 84 and the hub 80 can be sealed to prevent leakage either from the chamber 82 or into the chamber 82 by one or more sealing elements 96. The sealing elements 96 can comprise any number of suitable elements, such as O-rings, bushings, washers, molded elements or similar sealing elements. In yet other exemplary embodiments of the present invention, a U or cup shaped, X shaped or other type of wipe seal can be used, and provide additional benefits in that the sealing forces are reduced. The sealing elements 96 can be further configured to control the slidable movement of the catheter 84 by providing a degree of friction between the planar member 86 of the catheter 84 and the walls of the opening 88 of the hub 80. The hub 80 can further comprise elements such as the adhesive layer 74 to secure the hub to a skin surface for use.

In an exemplary embodiment of the present invention, the planar member 86 can be circular, oval, or any shape desired to provide the needed degrees of movement. In an exemplary embodiment of the present invention the planar member 86 can comprise a substantially circular element having a diameter of any suitable size, but preferably between 1.0 mm to 10.0 mm and a thickness of between 0.5 mm to 1.0 mm. Accordingly, the bottom opening 98 can have a diameter between 1.0 mm to 5.0 mm. In embodiments of the present invention, the bottom opening 98 can be circular, oval, or any shape desired to provide the needed degrees of movement.

Figure 9:
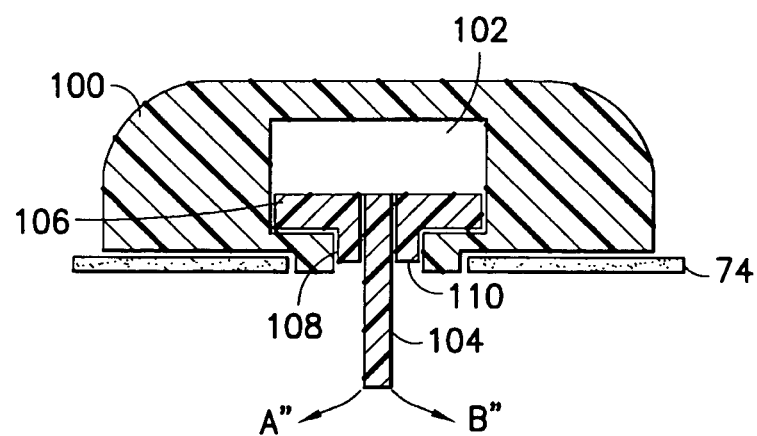
FIG. 9 is an enlarged cross-sectional view of an exemplary catheter and hub flexible union engagement comprising a bushing junction to provide a flexible connection in accordance with yet another embodiment of the present invention.

In yet another example, FIG. 9 shows an enlarged cross-sectional view of a hub, such as provided with a patch pump, incorporating an exemplary catheter and hub engagement comprising a flexible bushing junction in accordance with yet another embodiment of the present invention. In FIG. 9, a hub 100 is shown having a fluid, medication or other content storing reservoir 102 positioned above or in fluid communication with a catheter 104. A flexible bushing 106 can be secured or otherwise formed at one end of the catheter 104, and is provided to rotatably and/or slidably secure the catheter 104 with the lower surface of the hub 100.

Specifically, a lower portion of the hub body or reservoir 102 can comprise an opening into which the flexible bushing 106 can be captured. The opening can be sized to allow the flexible bushing 106 to be press fit into and thereafter captured by the lower portion of the reservoir 102. The flexible bushing 106 may also be captured within the hub 100 through the assembly of the hub body or in a similar manner. In doing so, the catheter 104 is free to move in a number of directions, such as those illustrated by the directions of arrows A" and B". That is, the catheter 104 of FIG. 9 is free to rotate to the extent permitted by the flexibility of the flexible bushing 106 and a bottom opening 110 in the lower surface of the body of the hub 100.

In an exemplary embodiment of the present invention, the flexible bushing 106 can comprise an outer diameter sufficient to be captured at a lower portion of the reservoir 102. The bushing 106 can further comprise a reduced portion 108 having an outer diameter sufficient to be captured within and seal the opening 110. To do so, exemplary embodiments of the bushing 106 can be comprised of a soft, low durometer, flexible material, which can also be configured to create the fluid seal, and which creates a flexible joint between the catheter 104 and the pump body or hub 100.

The catheter 104 can comprise any suitable catheter, such as those described above. The flexible bushing 106 can further comprise an opening therethrough to allow uninterrupted fluid communication during rotation and/or sliding, and at each rotated or slid position. Further, the junction between the catheter 104 and the flexible bushing 106, and between the flexible bushing 106 and the hub 100 can be sealed to prevent leakage either from the chamber 102 or into the chamber 102 by selection of the materials of the flexible bushing 106 and/or by the selection of materials securing the flexible bushing 106 within the hub 100. The hub 100 can further comprise elements such as the adhesive layer 74 to secure the hub to a skin surface for use.

In an exemplary embodiment of the present invention, the flexible bushing 106 can be circular, oval, or any shape desired to provide the needed degrees of movement. In an exemplary embodiment of the present invention the flexible bushing 106 can comprise a substantially circular element having diameter of any suitable size, but preferably between 2.0 mm to 10.0 mm, and a diameter at the reduced portion 108 between 1.0 mm to 9.0 mm. Accordingly, the bottom opening 110 can have a diameter between 1.0 mm to 9.0 mm. In embodiments of the present invention, the bottom opening 110 can be circular, oval, or any shape desired to provide the needed degrees of movement.

In each exemplary embodiment of the present invention described above, materials can be used which are compatible with both the contents of the device and which exhibit sufficient shelf life and sterilization qualities as required. In doing so, the exemplary embodiments of the present invention can provide a flexible union between the catheter and the hub.

As noted above, infusion sets and patch pumps are typically applied to a user's skin and have catheters that extend through the user's skin and into the subcutaneous tissue or other tissue, depending upon the specific use in either subcutaneous (SC) infusions, intradermal (ID) infusions, intramuscular (IM) infusions, and intravenous (IV) infusions. The catheters provide a fluid pathway for delivery of medication, such as insulin, into the tissue. The above described exemplary embodiments of the present invention enable the catheter, which is embedded in the user's skin and tissue, to move either as a flexible catheter or move relative to the hub, which is affixed to the user's skin. To do so, the catheter can be provided with channels, grooves and coatings such as a flexible sleeve or over-molded coating/sleeve, and the junction of the catheter to the hub can be comprised of a ball-and-socket joint, a sliding plate, a flexible bushing, or similar design, to enable the catheter to move and move relative to the hub. In each case, the junction can be further configured to be sealed to prevent leakage of contents through the junction.

Further, where the catheter is provided with both flexible and rigid features, and the sharpened, self-piercing tip, thereby allowing the insertion of the catheter without the use of an insertion needle, the catheter can act as the insertion needle and can remain in-dwelling, thereby further reducing the complexity of the insertion step.

Still further embodiments of the present invention can comprise an exemplary two-part hub with a flexible catheter as part of one infusion device. In an exemplary embodiment shown in FIG. 10, a device having two separate hubs as part of one infusion device, such as the outer hub and the catheter hub, can each be attached to the surface of the skin with a separate adhesive and the insulin flow between the two is preferably accomplished through a flexible fluid line or other similar connections means to isolate shock or applied forces from the external surface of the outer hub to the catheter. The two hubs, which can be attached to the surface of the skin as a single device, can be further configured such that the inner hub maintains the catheter position relative to the tissue in which the catheter has been inserted, and thereby reduce and eliminate irritation of the tissue and the cascade of events resulting from a foreign body response.

For example, such a device 120 is shown in FIG. 10 and comprises a housing 122 and housing adhesive 124, and a needle hub 126 and needle hub adhesive 128. A flexible connection 130 is provided between the outer housing 122 and the needle hub 126. A minimal gap 132 is provided between the outer housing 122 and the needle hub 126, such that the outer housing 122 can provide an envelope for the attachment and location of the needle hub 126 therein, but any force or movement conveyed to the outer housing 122 is not transferred to the needle hub 126.

Accordingly, the embodiment comprises a single device having two separate hubs 122 and 126 as part of one infusion device 120, wherein each can be attached to the surface of the skin with separate adhesive layers 124 and 128 and the insulin flow between the two is accomplished through the flexible fluid line or other similar connections means 130 to isolate shock or applied forces from the external surface of the outer hub 122 to the catheter 134. The two hubs 122 and 126 can be attached to the surface of the skin as a single device, and can be configured such that the inner hub 126 maintains the catheter 134 position relative to the tissue in which the catheter 134 has been inserted, and thereby reduce and eliminate irritation of the tissue and the cascade of events resulting from a foreign body response.

Figure 11:
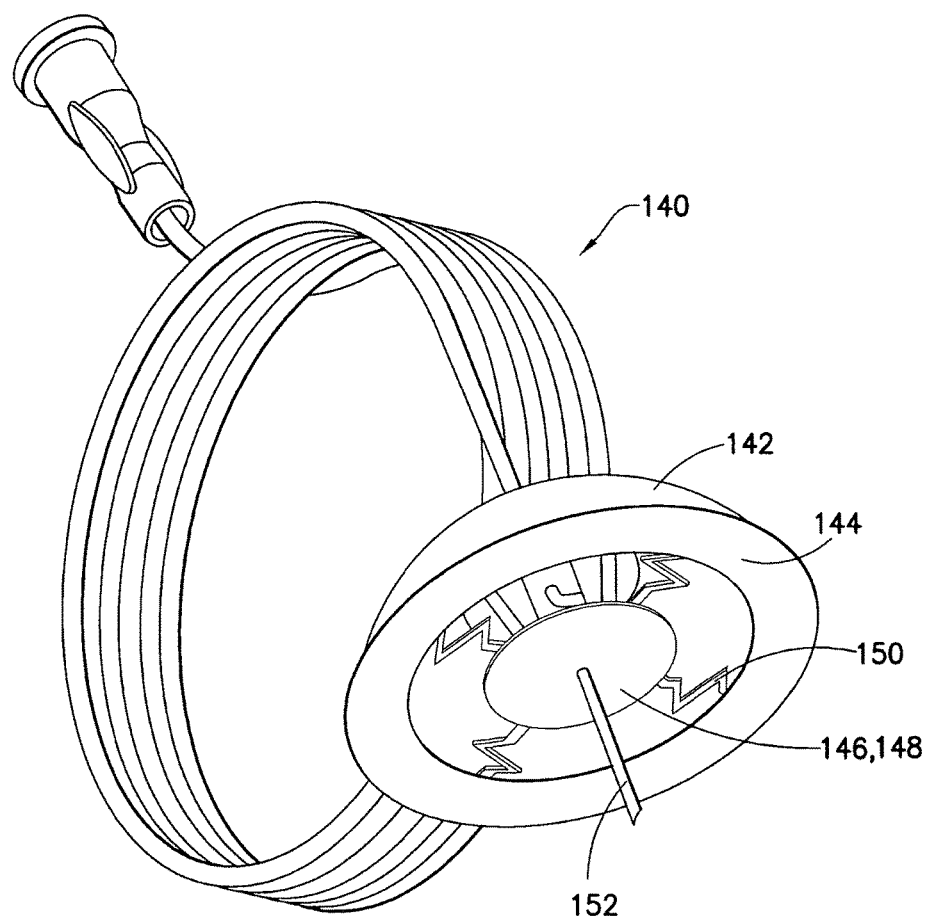
FIG. 11 is an enlarged cross-sectional view of an exemplary two-part hub with a flexible catheter in accordance with yet another embodiment of the present invention.

Another exemplary embodiment of the present invention providing such a two-part hub with a flexible catheter is illustrated in FIG. 11. The device 140 of FIG. 11 comprises a housing 142 and housing adhesive 144, and a needle hub 146 and needle hub adhesive 148. A flexible connection 150 is provided between the outer housing 142 and the needle hub 146, such that the outer housing 142 can provide an envelope for the attachment and location of the needle hub 146 therein, but any force or movement conveyed to the outer housing 142 is not transferred to the needle hub 146 and catheter 152.

Still further, the exemplary embodiments of the present invention described above can be used in a device with one or more additional features for the retraction of the insertion cannula or in-dwelling catheter either within a sleeve or over a sleeve to cover the sharp edge of the insertion cannula or in-dwelling catheter. FIGS. 12A and 12B, and FIGS. 13A and 13B are enlarged cross-sectional views of exemplary hub devices with a retractable insertion cannula or in-dwelling catheter that is either flexible or rigid in nature, in accordance with another embodiment of the present invention.

Figure 12A:
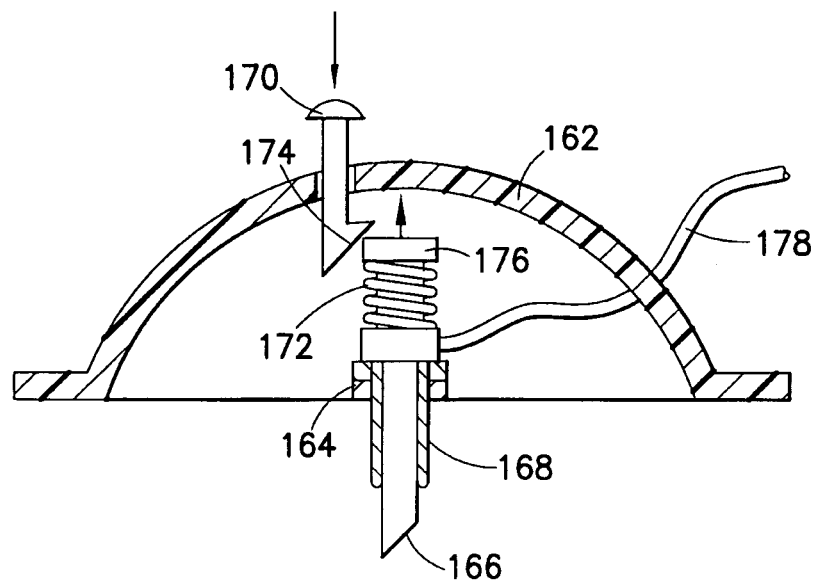
FIGS. 12A and 12B are an enlarged cross-sectional views of an exemplary hub with a retractable insertion catheter that is either flexible or rigid in nature, in accordance with another embodiment of the present invention.

As shown in FIG. 12A, the device 160 can comprise an outer hub 162, inner hub 164, retractable insertion cannula or in-dwelling catheter 166, and a blunt cannula 168. A retraction system comprising a push button or other lever 170 can be provided through the outer hub 162 to secure and then release the insertion cannula or in-dwelling catheter 166 as urged by a biasing element such a spring. The button 170 can comprise a shoulder, detent or other similar element to hold a position of the insertion cannula or in-dwelling catheter 166 through contact, such as the contact between detent 174 and shoulder 176 of the insertion cannula or in-dwelling catheter 166.

When pressed, the button 170 releases the shoulder 176 and the insertion cannula or in-dwelling catheter is urged upward by the spring 172 for a short distance, thereby shielding the sharpened end of the insertion cannula or in-dwelling catheter within the blunt cannula 168. Fluid communication to the insertion cannula or in-dwelling catheter is then achieved through the connection of tubing 178.

Figure 12B:
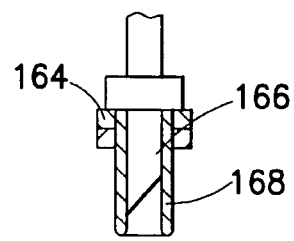

In the embodiment shown in FIG. 12A, the insertion cannula or in-dwelling catheter 166 is retracted upward within the blunt cannula 168 as shown in the retracted illustration of FIG. 12B.

Figure 13A:
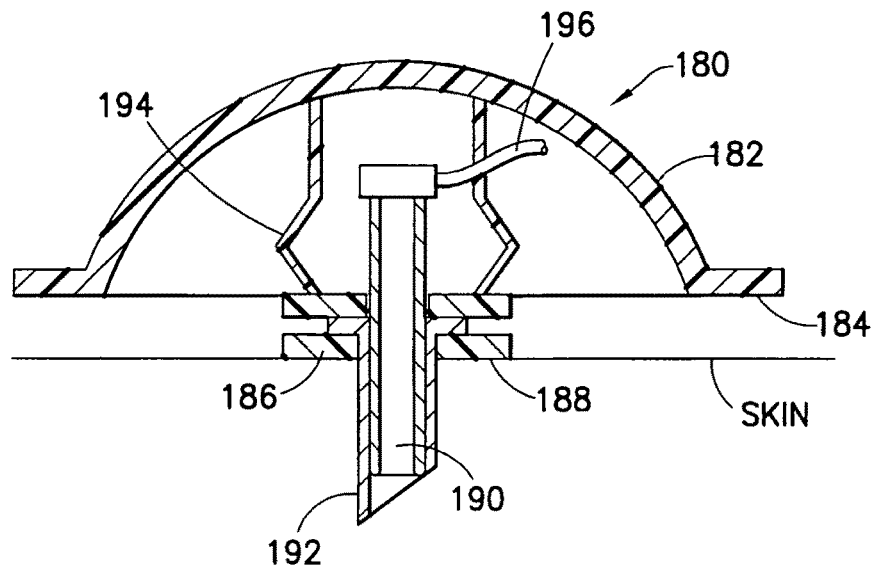
FIGS. 13A and 13B are enlarged cross-sectional views of an exemplary hub with a retractable insertion catheter that is either flexible or rigid in nature, in accordance with yet another embodiment of the present invention.
Figure 13B:
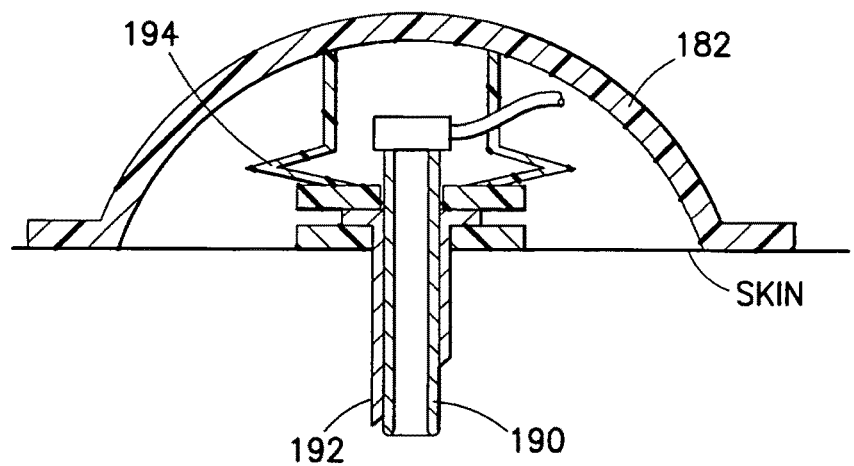

A second exemplary embodiment is shown in FIG. 13A, wherein the device 180 can comprise an outer hub 182 and outer hub adhesive layer 184, inner hub 186 and inner hub adhesive layer 188, blunt cannula 190, and a retractable insertion cannula or in-dwelling catheter 192. A retraction system is activated by simply pressing down on the outer hub 182. As shown in FIG. 13B, when the outer hub 182 is pressed down to be affixed to the skin surface, the over-center hinges 194 permit travel of the inner hub 186 which retracts the retractable insertion cannula or in-dwelling catheter 192 over the blunt cannula 190 such that the sharpened end of the insertion cannula or in-dwelling catheter is raised above the end of the blunt cannula 190 as shown in FIG. 13B. Fluid communication to the catheter is then achieved through the connection of tubing 196. The inner hub 186 can further comprise any number of suitable sealing elements between inner and outer needles using for example, a seal or lubricant.

Figure 14:
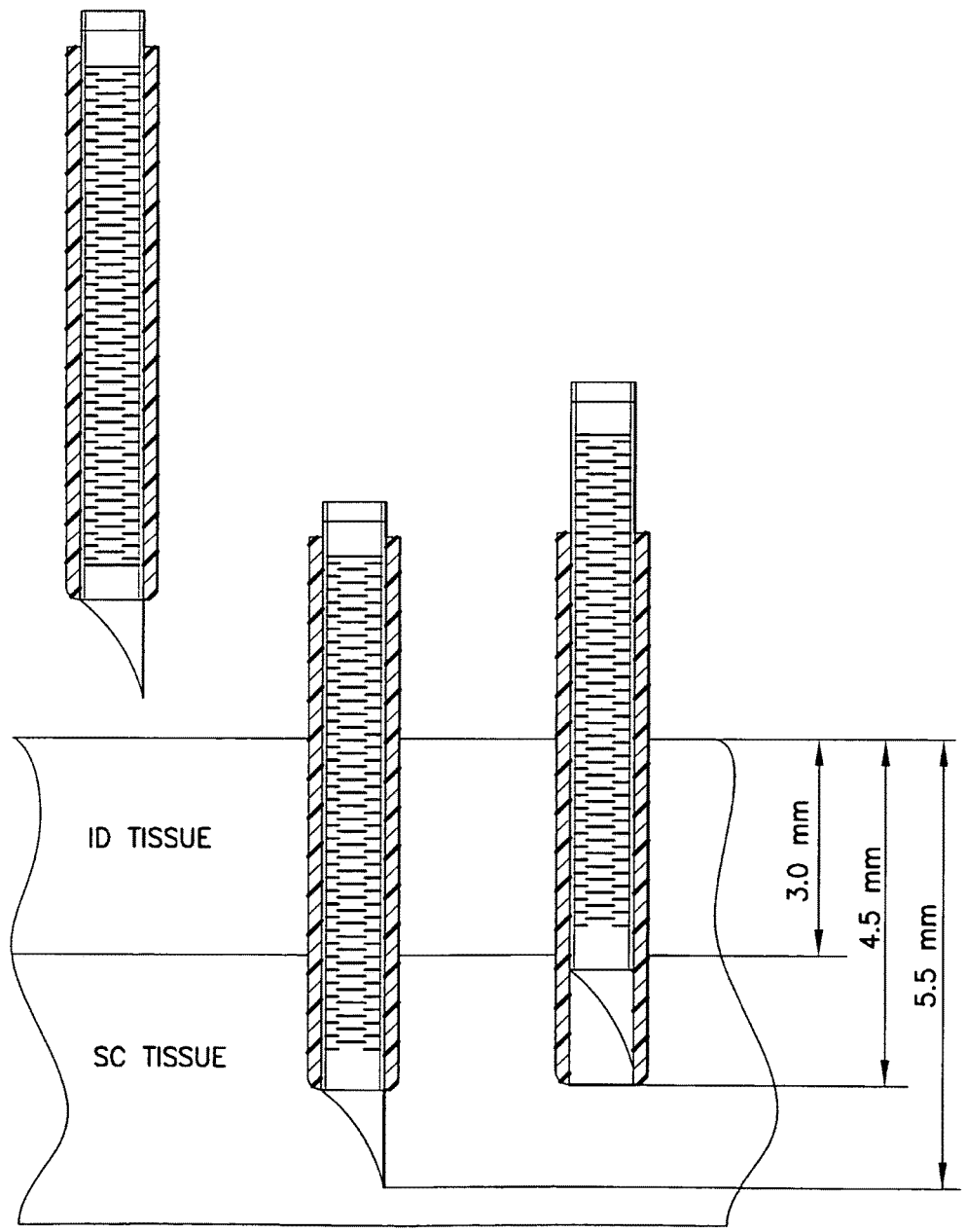
FIG. 14 illustrates the slight retraction of the insertion catheter that is either flexible or rigid in nature, within a sleeve to protect a sharpened end.

FIG. 14 illustrates such a partially retracting needle concept wherein the insertion cannula or in-dwelling catheter that is either flexible or rigid in nature, is shown in a pre-use position with a sharpened end exposed, a post-use position where the insertion cannula or in-dwelling catheter and sleeve are shown in an SC tissue position, and in a retracted position wherein the insertion cannula or in-dwelling catheter is retracted within the outer sleeve a distance sufficient to cover the sharpened end of the insertion cannula or in-dwelling catheter. By partially removing the insertion cannula or in-dwelling catheter after inserting the insertion cannula or in-dwelling catheter, the sharpened end of the insertion cannula or in-dwelling catheter is no longer exposed and allowed to irritate the SC tissue. Further, kinking of the Teflon® or Vialon® insertion cannula or in-dwelling catheter can be reduced by leaving the insertion cannula or in-dwelling catheter in the outer sheath in the inserted position. Although the embodiment of FIG. 14 is shown in use in a subcutaneous (SC) infusion, the embodiment can also be used in intradermal (ID) infusions, intramuscular (IM) infusions, and intravenous (IV) infusions. Further, the in-dwelling catheter shown in FIG. 14 can be either rigid/solid (i.e. without slots), or flexible (i.e. with slots).

A further embodiment is shown in FIG. 15 wherein the catheter is configured to provide infusion to both intradermal (ID) tissue and subcutaneous (SC) tissue, either simultaneously or each intermittently as required to satisfy the drug delivery needs of the patient. As described in the previous embodiments, the insertion cannula retracts to protect the tissue from the sharp edges of the needle tip, after placing the catheter into the tissue. The insertion cannula or introducer needle in FIG. 15 is shown in the retracted position, and the needle is formed in a manner to provide two distinct fluid paths in combination with the polymer outer sleeve.

Figure 15A:
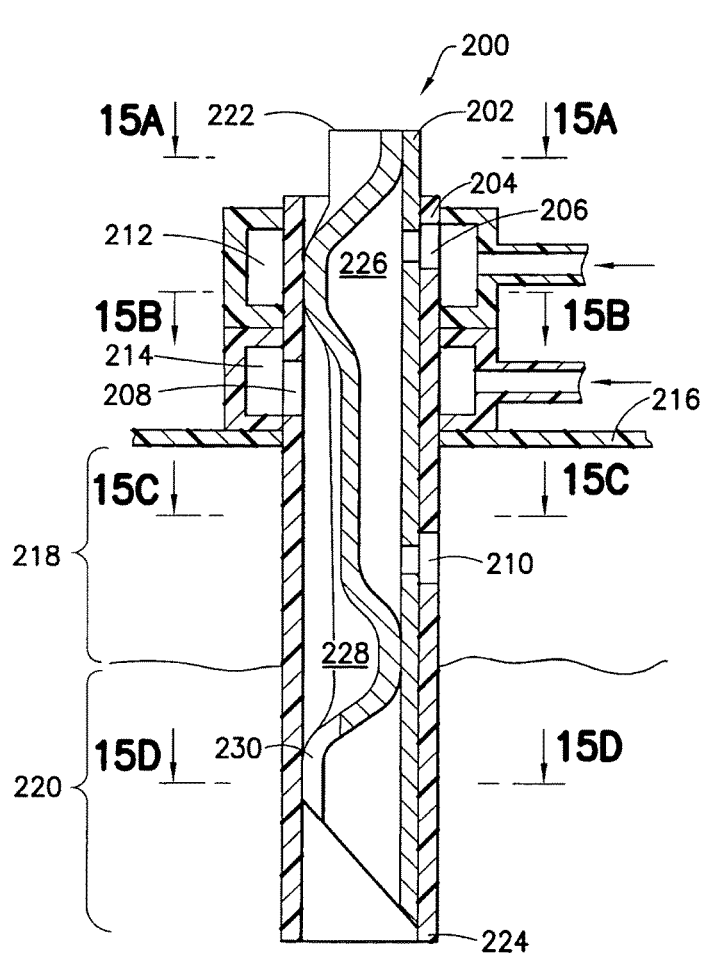
FIG. 15A is an enlarged cross-sectional view of an exemplary infusion catheter with formed rigid internal lumens and external polymer sleeve in accordance with yet another embodiment of the present invention.
Figure 15B:
FIGS. 15B-15E are sectional views of the infusion catheter taken along the lines A-A, B-B, C-C, and D-D of FIG. 15A, respectively.
Figure 15C:
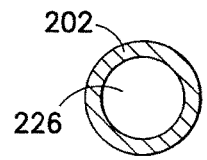
Figure 15D:
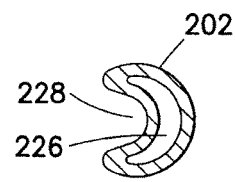
Figure 15E:
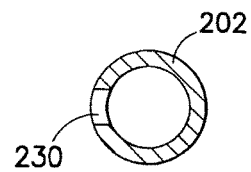

In the exemplary embodiment shown in FIG. 15A, a device 200 is shown including a formed cannula such as the exemplary steel cannula 202, over which a sleeve such as the polymer sleeve 204 is formed, and which are further aligned in a manner to provide fluid communication between each, via a cross-port 206, 208 and 210. The cross-port 206 is provided to be in fluid communication with chamber 212, and the cross-port 208 is provided to be in fluid communication with chamber 214. In the exemplary embodiment shown, the chamber 212 is in fluid communication with a first reservoir providing for example, a fast-acting medicament, and the chamber 214 is in fluid communication with a second reservoir providing for example, a slow-acting medicament (see for example, FIG. 16). Each element can be supported within or upon an infusion hub 216.

As described in greater detail below, the device 200 of FIG. 15A can be placed upon an insertion site to reach the ID tissue space 218 and an SC tissue space 220. In the exemplary embodiment shown, the cross-port 210 is configured to access the ID tissue space 218, and an open proximal end of the steel cannula 202 and the polymer sleeve 204 is configured to access the SC tissue space 220. Specifically, the steel cannula 202 is crimped fully closed at a distal end 222 shown by view A-A of FIG. 15B, fully uncrimped at a point shown by view B-B of FIG. 15C, partially crimped at a point shown by view C-C of FIG. 15D, and fully uncrimped at a point shown by view D-D of FIG. 15E, and wherein at least the further opening 230 is provided. In doing so, the single steel cannula 202 and polymer 204 create first and second flow paths 226 and 228, wherein flow path 226 is configured to provide communication between the cross-port 206 and the cross-port 210, and the flow path 228 is configured to provided communication between the cross-port 208 and the open proximal end 224 via the opening 230. The steel cannula can be sharpened at this end as shown, or can be blunt.

The first path 226 which provides fluid to the intradermal (ID) tissue 218 is through the cross-port 206 in the cannula 202 which aligns with a similar opening in the polymer sleeve 204, when the cannula 202 is in the retracted position. The fluid path 226 continues through the internal lumen of the cannula 202 and exits through a similar cross-port 210 into the intradermal (ID) tissue 218. The second fluid path 228 is through the cross-port 208 in the external polymer sleeve 204 and continues in the lumen created between the inner surface of the polymer sleeve 204 and the outer surface of the cannula 202, and exits out through the end 224 of the catheter into subcutaneous (SC) tissue 220. This alternative embodiment enables infusion into at least two sites, e.g. intradermal (ID) tissue and subcutaneous (SC) tissue, each tissue having distinctive behavior for insulin up-take as described in U.S. Patent Publication No. 2002/0095134, of Pettis et al., the entire disclosure of which being expressly incorporated herein by reference.

With infusion pump therapy, basal insulin infusion is continuous throughout the day with subtle changes in the infusion rate to compensate for changes in activity and stress. Traditionally, basal requirements have been satisfied by slow-acting insulin. Bolus insulin infusion is used to compensate for carbohydrate consumption at meals and also to correct for high blood glucose, i.e. hyperglycemia. Fast-acting insulin provides the best therapy for bolus infusion. Insulin up-take is much faster in intradermal (ID) tissue as compared to subcutaneous (SC) tissue. Therefore, the exemplary embodiment shown in FIG. 15A can be used to infuse fast-acting insulin into the intradermal (ID) tissue for bolus requirements and infuse slow-acting insulin into subcutaneous (SC) tissue for basal requirements.

Figure 16:
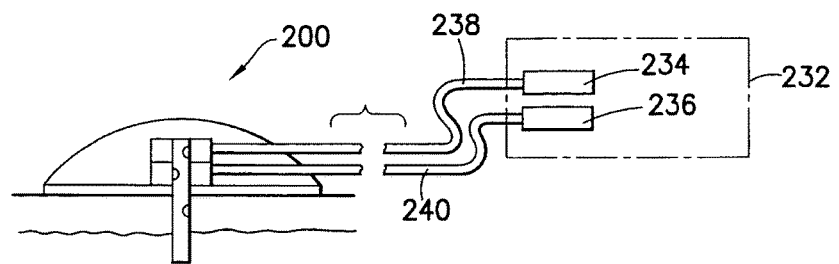
FIG. 16 illustrates an exemplary infusion pump with dual reservoirs and a dual lumen infusion set in accordance with an embodiment of the present invention.

As shown in FIG. 16, an exemplary infusion pump 232 is shown that is configured to support the device 200 of FIG. 15A. The infusion pump 232 can incorporate at least two reservoirs 234 and 236, one for fast-acting insulin and a second for slow-acting insulin. The infusion set can further provide two separate lumens 238 and 240, which would connect to the separate chambers within the set hub. In yet another exemplary embodiment of the present invention, the two separate lumens 238 and 240 can be incorporated into a single lumen with multiple channels (not shown).

Figures 17A, 17B:
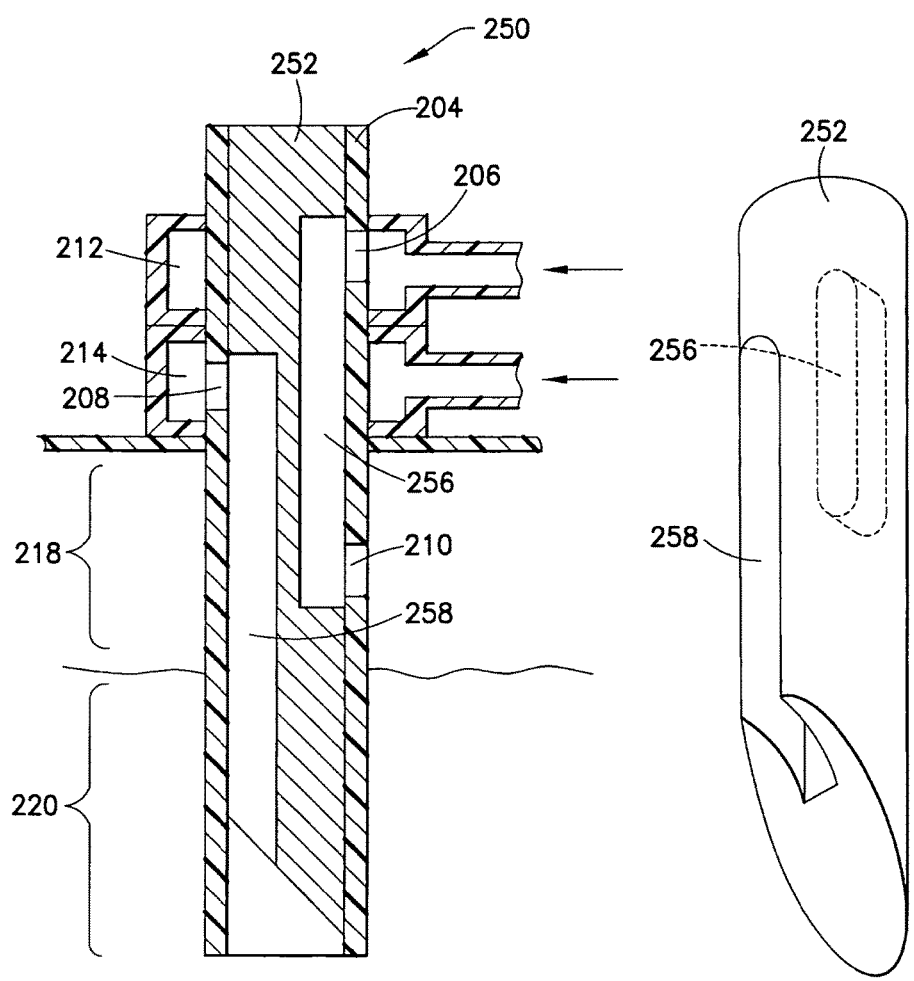
FIG. 17A is an enlarged cross-sectional view of an exemplary infusion catheter cast, molded or machined from a solid rod in accordance with an embodiment of the present invention.
FIG. 17B is a perspective view of the infusion catheter of FIG. 17A.

Yet another exemplary embodiment of the present invention can include a formed cannula as shown in FIG. 17A, wherein the cannula has been replaced with a solid rod into which two channels have been formed or machined. Specifically, the cannula of the device 250 has been replaced with a solid rod 252 into which two channels 256 and 258 have been formed or machined. The remaining features are substantially as described in regard to FIG. 15A. The cross-ports 206 and 208 in the external polymer sleeve 204 in combination with the channels 256 and 258 provide two separate fluid pathways to deliver different or similar drugs to the intradermal (ID) tissue and subcutaneous (SC) tissue in a manner substantially similar to that of FIG. 15A. A perspective view of the exemplary solid rod 252 into which two channels 256 and 258 have been formed or machined is shown in FIG. 17B. As with the exemplary embodiments described above, the rod 252 can be sharpened at the end as shown, or can be blunt.

Figure 18A:
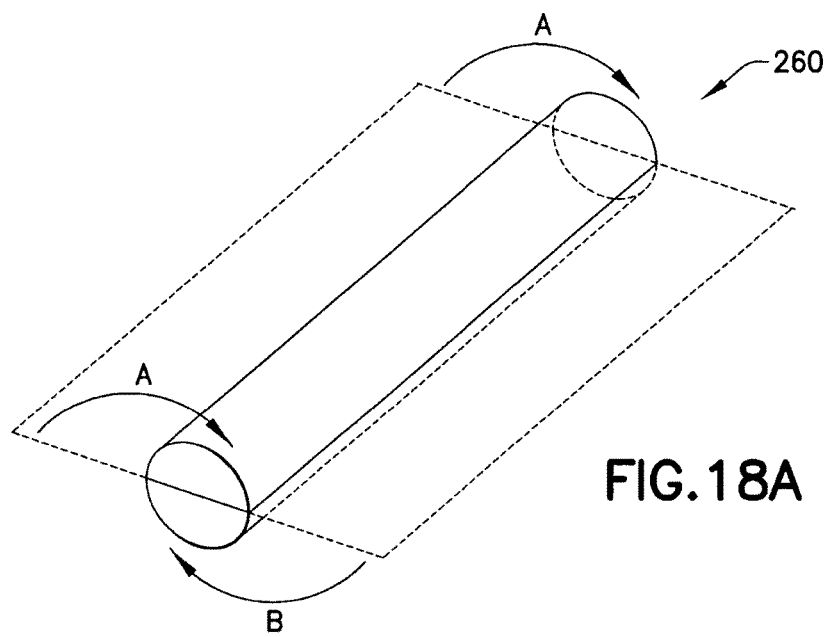
FIGS. 18A-18E illustrate an exemplary infusion catheter and forming sequence to produce such a multi-lumen cannula from a flat sheet in accordance with an embodiment of the present invention.
Figure 18B:
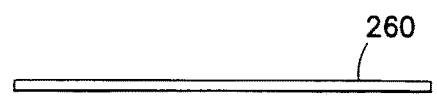
Figure 18C:
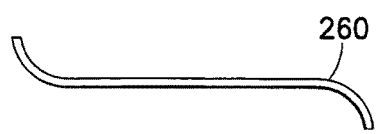
Figure 18D:
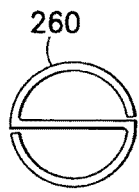
Figure 18E:
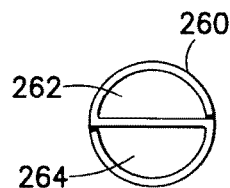

In yet another embodiment, shown in FIGS. 18A-18E, a dual lumen catheter or cannula 260 can be formed from a flat sheet of any suitable material as shown in FIG. 18B, rolled in the direction of arrows A and B as shown in FIG. 18C until substantially reaching a final desired shape as shown in FIG. 18D, and then either welded to close and seal the lumens as shown in FIG. 18E, or captured within an external polymer sleeve (not shown), such that two separate fluid pathways 262 and 264 are provided to deliver different or similar drugs to the intradermal (ID) tissue and subcutaneous (SC) tissue. Alternately, the dual lumen cannula 260 can be extruded or injection molded into a form that is similar to those shown in FIGS. 17A-17B and 18A-18D. For example, the extrusion process would produce a continuous cross-section, similar to that shown in FIG. 18E. Injection molding could be utilized to produce the cannula shown in FIGS. 17A and 17B.

Figure 19:
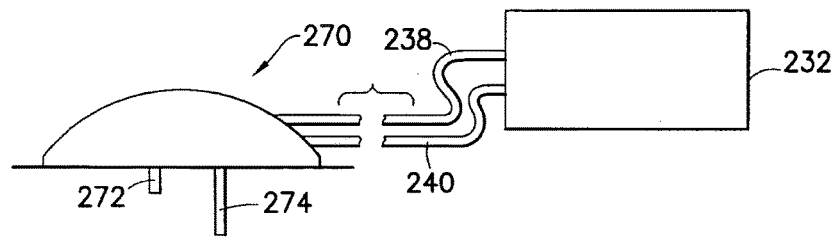
FIG. 19 illustrates an exemplary infusion pump with two catheters, one for infusion into intradermal (ID) tissue and one for infusion into subcutaneous (SC) tissue in accordance with an embodiment of the present invention.

In still another exemplary embodiment of the present invention shown in FIG. 19, two or more separate catheters can be used to provide the desired two or more separate fluid pathways to deliver different or similar drugs to the intradermal (ID) tissue and subcutaneous (SC) tissue. The exemplary embodiment shown in FIG. 19 includes the device 270 having the two separate catheters 272 and 274, and is shown connected to the exemplary infusion pump 232 incorporating at least two reservoirs, one for fast-acting insulin and a second for slow-acting insulin. In the exemplary embodiment shown, the catheter 272 can be provided for targeting the ID tissue, and the catheter 274 can be provided for targeting the SC tissue.

Figure 20:
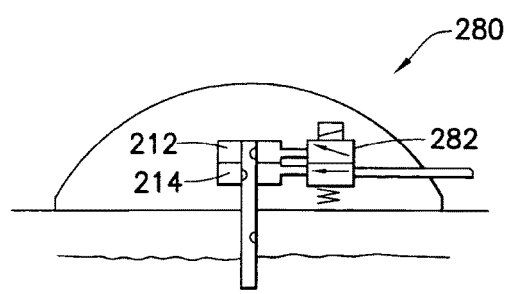
FIG. 20 illustrates an exemplary infusion pump and set with an electronically controlled valve to selectively direct infusion to either the intradermal (ID) tissue, the subcutaneous (SC) tissue, or both the intradermal (ID) tissue and subcutaneous (SC) tissue in accordance with an embodiment of the present invention.

Currently marketed insulin infusion pumps only have a single reservoir, and fast-acting insulin is typically used to reduce complications from overlapping doses. Although the use of these pumps does not allow combination drug therapy, e.g. fast-acting insulin infusion in combination with slow-acting insulin infusion, many of the benefits stated above can be realized by infusing fast-acting insulin to both the intradermal (ID) tissue and subcutaneous (SC) tissue. Since it is preferred to infuse bolus dosages into the intradermal (ID) tissue and basal infusion into the subcutaneous (SC) tissue, in yet another exemplary embodiment of the present invention a valve arrangement can be provided, such as with the infusion hub, to redirect the high-pressure bolus dose to the intradermal (ID) tissue. FIG. 20 illustrates an exemplary hub 280 having such a valve 282 disposed within the hub and coupled between the first and second chambers 212 and 214, and the infusion pump (not shown). The valve can be any suitable valve, such as the solenoid activated valve 282 shown in FIG. 20. For example the valve shown is a two-position, solenoid operated, spring return valve. The valve is shown in the normal, i.e. spring return, state, which would correspond with infusion into the subcutaneous (SC) tissue. Actuating the solenoid would shift the valve to allow flow to intradermal (ID) tissue.

In use, the device 280 can be used to redirect flow utilizing the electronically operated valve 282 as shown in FIG. 20, which could operate from a wireless signal, such as those described in U.S. patent application Ser. No. 12/458,807, of Searle et al., filed Jul. 23, 2009, the entire disclosure of which being expressly incorporated herein by reference, or a signal transmitted over an electrical line that is incorporated into the infusion set and allows the controller in the pump to communicate with the electronic valve in the infusion set hub. The electrical line could also be utilized to provide communication from a sensor, e.g. a blood glucose sensor, to the controller in the pump. The valve 282 can be further provided with a manual activation button to allow the user to manually shift the valve as described.

Figure 21A:
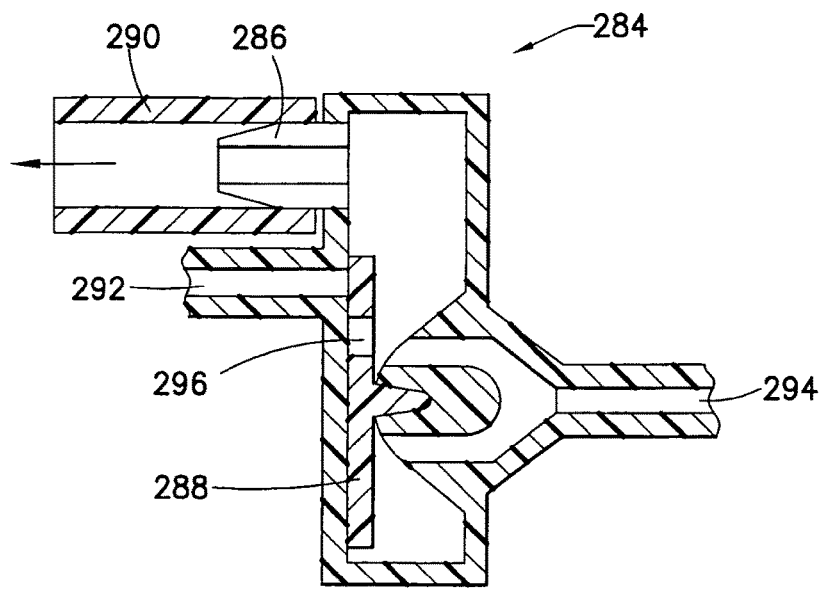
FIG. 21A illustrates an exemplary fluidic valve configuration that selectively directs low-pressure flow to subcutaneous (SC) tissue and high-pressure flow to intradermal (ID) tissue in accordance with an embodiment of the present invention, wherein the valve configuration is shown in the high-pressure state.

In yet another exemplary embodiment of the present invention, a valve system can be configured as shown in FIG. 21A, to redirect the high pressure bolus dose to the intradermal (ID) lumen of the catheter and following completion of the bolus infusion, as the pressure drops, direct the low-pressure basal infusion to the subcutaneous (SC) lumen of the catheter. In the valve configuration 284 shown in FIG. 21A, an umbrella check valve 286 is used in combination with a duck-bill check valve 288, but is not limited thereto.

Figure 21B:
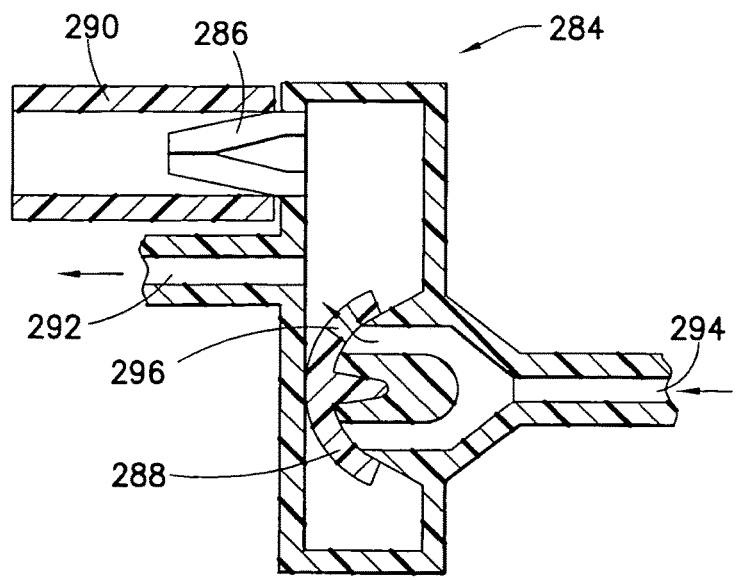
FIG. 21B illustrates the fluidic valve configuration of FIG. 21A with the valve configuration shown in the low pressure state.

In the exemplary embodiment shown in FIGS. 21A-21B, the port or hole 296 in the umbrella check valve 288 allows insulin that enters opening 294 as the basal or low-pressure flow from the infusion pump (not shown), to flow through and enter the subcutaneous (SC) lumen 292 of the catheter (not shown), while the fluid pressure is low as shown in FIG. 21B. In this position, the duck-bill check valve 286 is closed preventing flow through the intradermal (ID) lumen 290 of the catheter.

When the fluid pressure exceeds the cracking pressure of the umbrella and duck-bill check valves, i.e. during bolus infusion, the umbrella check valve 288 opens, blocking the subcutaneous (SC) lumen pathway 292 as shown in FIG. 21A, and the duck-bill check valve 286 opens allowing flow through the intradermal (ID) lumen 290 of the catheter. Following bolus delivery, the pressure reduces and allows the duck-bill and umbrella check valves to reset to their normally closed condition, i.e. to allow basal flow through the subcutaneous (SC) lumen 292 of the catheter as shown in FIG. 21B. In doing so, the pressures associated with the desired infusion are used as the valve control in the exemplary embodiments.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

What is claimed is:

1. An infusion device, comprising:
a catheter body extending between distal and proximal ends, comprising an axis extending between said distal and proximal ends, and one or more axial openings parallel to said axis, and one or more radial openings perpendicular to said axis, passing through at least a portion of said catheter body,
wherein said catheter body comprises a flexible element for flexibly coupling an indwelling portion of the catheter body to a hub of an infusion set or patch pump device, the hub comprising a skin attachment surface comprising an adhesive for attaching the skin attachment surface to a skin surface; and
wherein said catheter body comprises:
a first catheter body portion comprising a first flow path configured to target a first tissue space; and
a second catheter body portion comprising a second flow path configured to target a second tissue space.

2. The infusion device as claimed in claim 1, wherein said catheter body comprises a plurality of separated radial openings passing through at least a portion of said catheter body to target the first tissue space, and the second tissue space, respectively.

3. The infusion device as claimed in claim 1, wherein said infusion device further comprises:
a flexible catheter body portion, comprising a catheter body wall wherein one or more lengths of said wall are provided with one or more channels, grooves, or separations, extending between said one or more axial openings and an outer surface of said catheter body.

4. The infusion device as claimed in claim 3, wherein said catheter body further comprises a coiled spring, and said separations comprise contacting adjacent coils created by said coiled spring of said catheter body.

5. The infusion device as claimed in claim 3, wherein:
said catheter body is substantially closed at said distal end; and
at least one of said channels, grooves, or separations are configured to provide fluid communication between said one or more axial openings and said outer surface of said catheter body.

6. The infusion device as claimed in claim 1, wherein said catheter body further comprises an outer sheath disposed upon at least a portion of said catheter body.

7. The infusion device as claimed in claim 6, wherein said outer sheath comprises at least one of a Teflon® outer coating layer disposed over a portion of said catheter body, and a Vialon® outer coating layer disposed over a portion of said catheter body.

8. The infusion device as claimed in claim 1, wherein the catheter body comprises a beveled surface configured to pierce an insertion site during insertion.

9. The infusion device as claimed in claim 1, wherein said catheter further comprises a heparin coating, or one of a family of anti-coagulants, disposed upon at least a portion of said catheter body.

10. The infusion device as claimed in claim 1, wherein said element of said catheter body for flexibly coupling said portion of said catheter body to said hub comprises:
a flexible union element at said proximal end of said catheter body, configured to flexibly couple said proximal end of said catheter body with said hub.

11. The infusion device as claimed in claim 10, wherein said flexible union element comprises at least one of a:
a ball element, wherein said ball element is configured to be rotatably captured within said hub to provide said flexible union;
a sliding plate, wherein said sliding plate is configured to be slidably captured within said hub to provide said flexible union;

a flexible bushing, wherein said flexible bushing is configured to be captured within said hub to provide said flexible union; and a bellows joint, wherein said bellows joint is configured to be secured to said hub to provide said flexible union.

12. The infusion device as claimed in claim 10, wherein said flexible union element at said proximal end of said catheter body further comprises at least one sealing element disposed between said catheter body and said hub.

13. The infusion device as claimed in claim 1, further comprising:

a hub body comprising an opening for flexibly coupling a portion of the catheter body.

14. The infusion device as claimed in claim 13, wherein said opening for flexibly coupling said hub to said catheter body comprises at least one of a:

a ball detent opening configured to rotatably secure a ball element of said catheter to provide said flexible union;

a chamber opening configured to slidably secure a sliding plate of said catheter to provide said flexible union;

a chamber opening configured to secure a flexible bushing of said catheter to provide said flexible union; and a bellows joint configured to secure said catheter to provide said flexible union.

15. The infusion device as claimed in claim 1, further comprising:

an infusion pump in fluid communication with the catheter body; and a valve to direct a bolus infusion from said infusion pump to a first tissue space and a basal infusion from said infusion pump to a second tissue space.

16. The infusion device as claimed in claim 1, further comprising:

an infusion pump, comprising a first reservoir configured to supply a first substance to a first tissue space through said catheter body, and a second reservoir configured to supply a second substance to a second tissue space through said catheter body.

17. The infusion device as claimed in claim 1, further comprising:

an infusion pump in fluid communication with the catheter body, comprising at least one reservoir configured to supply bolus delivery to a first tissue space, and at least one reservoir configured to supply basal delivery to a second tissue space, and a device for delivering the second substance to the second tissue space.

18. The device as claimed in claim 1, further comprising:

an infusion pump in fluid communication with the catheter body, comprising a single reservoir to supply bolus infusion to a first tissue space, and a basal infusion to a second tissue space, and a device for delivering the second substance to the second tissue space.

19. A dual-lumen infusion device, comprising:

a hub;

a dual-lumen catheter, comprising an axis extending between distal and proximal ends of said catheter, and comprising a plurality of axially separated openings in said catheter to target a first tissue depth, and a second tissue depth, respectively; and a valve, configured to direct a bolus infusion to a first opening of said dual-lumen catheter to target said first tissue depth, and direct a basal infusion to a second opening of said dual-lumen catheter to target said second tissue depth.

20. The dual-lumen infusion device as claimed in claim 19, wherein said dual-lumen catheter comprises a first catheter body configured to target a first tissue depth, and a second catheter body configured to target a second tissue depth.

21. The dual-lumen infusion device as claimed in claim 19, further comprising an infusion pump, comprising at least one reservoir configured to supply fast-acting insulin to said first tissue depth, and at least one reservoir configured to supply slow-acting insulin to said second tissue depth.

22. The dual-lumen infusion device as claimed in claim 19, further comprising an infusion pump, comprising at least one reservoir configured to supply bolus delivery to said first tissue depth, and at least one reservoir configured to supply basal delivery to said second tissue depth.

23. The dual-lumen infusion device as claimed in claim 19, further comprising an infusion pump, comprising a single reservoir to supply bolus infusion to said first tissue depth, and a basal infusion to said second tissue depth.

* * * * *